US010179241B2

United States Patent
Walker et al.

(10) Patent No.: US 10,179,241 B2
(45) Date of Patent: Jan. 15, 2019

(54) SYSTEMS AND METHODS FOR PRODUCING ASYNCHRONOUS NEURAL RESPONSES TO TREAT PAIN AND/OR OTHER PATIENT CONDITIONS

(71) Applicant: Nevro Corp., Redwood City, CA (US)

(72) Inventors: Andre B. Walker, Monte Sereno, CA (US); Zi-Ping Fang, Beachwood, OH (US); Anthony V. Caparso, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

(21) Appl. No.: 15/868,861

(22) Filed: Jan. 11, 2018

(65) Prior Publication Data

US 2018/0133483 A1    May 17, 2018

Related U.S. Application Data

(63) Continuation of application No. 15/192,914, filed on Jun. 24, 2016, which is a continuation of application
(Continued)

(51) Int. Cl.
*A61N 1/00* (2006.01)
*A61N 1/36* (2006.01)
(Continued)

(52) U.S. Cl.
CPC ....... *A61N 1/36171* (2013.01); *A61N 1/0551* (2013.01); *A61N 1/36071* (2013.01); *A61N 1/37247* (2013.01)

(58) Field of Classification Search
CPC .............. A61N 1/0551; A61N 1/36071; A61N 1/36171; A61N 1/37247
See application file for complete search history.

(56) References Cited

U.S. PATENT DOCUMENTS

| 1,597,061 A | 8/1926 | Cultra |
| 2,622,601 A | 12/1952 | Nemec |

(Continued)

FOREIGN PATENT DOCUMENTS

| DE | 10318071 | 11/2004 |
| EP | 1181947 | 2/2002 |

(Continued)

OTHER PUBLICATIONS

"Incredible Save Followed by Poor Communications" APSF Newsletter, pp. 63 and 64, Wnter 2005-2006.
(Continued)

*Primary Examiner* — George Manuel
(74) *Attorney, Agent, or Firm* — Perkins Coie LLP

(57) ABSTRACT

Systems and methods for producing asynchronous neural responses to treat pain and/or other patient conditions are disclosed. A method in accordance with a particular embodiment includes selecting a target stimulation frequency that is above a threshold frequency, with the threshold frequency corresponding to a refractory period for neurons of a target sensory neural population. The method can further include producing a patient sensation of paresthesia by directing an electrical signal to multiple sensory neurons of the target sensory neural population at the stimulation frequency, with individual neurons of the sensory neural population completing corresponding individual refractory periods at different times, resulting in an asynchronous sensory neuron response to the electrical signal.

22 Claims, 10 Drawing Sheets

Related U.S. Application Data

No. 14/483,061, filed on Sep. 10, 2014, now Pat. No. 9,403,013, which is a continuation of application No. 13/857,960, filed on Apr. 5, 2013, now Pat. No. 8,849,410, which is a continuation of application No. 13/544,727, filed on Jul. 9, 2012, now Pat. No. 8,509,906, which is a continuation-in-part of application No. 12/362,244, filed on Jan. 29, 2009, now Pat. No. 8,255,057.

(51) Int. Cl.
  *A61N 1/05* (2006.01)
  *A61N 1/372* (2006.01)

(56) References Cited

U.S. PATENT DOCUMENTS

| | | |
|---|---|---|
| 3,195,540 A | 7/1965 | Waller |
| 3,646,940 A | 3/1972 | Timm et al. |
| 3,727,616 A | 4/1973 | Lenzkes |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |
| 4,155,366 A | 5/1979 | Di Mucci |
| 4,289,136 A | 9/1981 | Rienzo, Sr. |
| 4,315,503 A | 2/1982 | Ryaby et al. |
| 4,379,462 A | 4/1983 | Borkan et al. |
| 4,414,986 A | 11/1983 | Dickhudt et al. |
| 4,441,498 A | 4/1984 | Nordling |
| 4,459,989 A | 7/1984 | Borkan |
| 4,535,777 A | 8/1985 | Castel |
| 4,541,432 A | 9/1985 | Molina-Negro et al. |
| 4,608,985 A | 9/1986 | Crish et al. |
| 4,612,934 A | 9/1986 | Borkan et al. |
| 4,649,935 A | 3/1987 | Charmillot et al. |
| 4,702,254 A | 10/1987 | Zabara |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill et al. |
| 5,188,104 A | 2/1993 | Wernicke et al. |
| 5,330,515 A | 7/1994 | Rutecki et al. |
| 5,335,657 A | 8/1994 | Terry, Jr. et al. |
| 5,417,719 A | 5/1995 | Hull et al. |
| 5,501,703 A | 3/1996 | Holsheimer et al. |
| 5,514,175 A | 5/1996 | Kim et al. |
| 5,540,730 A | 7/1996 | Terry, Jr. et al. |
| 5,540,734 A | 7/1996 | Zabara |
| 5,562,717 A | 10/1996 | Tippey et al. |
| 5,643,330 A | 7/1997 | Holsheimer et al. |
| 5,702,428 A | 12/1997 | Tippey et al. |
| 5,707,396 A | 1/1998 | Benabid |
| 5,716,377 A | 2/1998 | Rise |
| 5,733,322 A | 3/1998 | Starkebaum |
| 5,776,170 A | 7/1998 | MacDonald et al. |
| 5,792,187 A | 8/1998 | Adams |
| 5,830,151 A | 11/1998 | Hadzic et al. |
| 5,853,373 A | 12/1998 | Griffith et al. |
| 5,893,883 A | 4/1999 | Torgerson et al. |
| 5,895,416 A | 4/1999 | Barreras |
| 5,925,070 A | 7/1999 | King et al. |
| 5,938,690 A | 8/1999 | Law |
| 5,948,007 A | 9/1999 | Starkebaum et al. |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,035,657 A | 3/2000 | Dobak, III et al. |
| 6,104,957 A | 8/2000 | Alo et al. |
| 6,161,044 A | 12/2000 | Silverstone |
| 6,161,048 A | 12/2000 | Sluijter et al. |
| 6,167,305 A | 12/2000 | Cammilli et al. |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,381,496 B1 | 4/2002 | Meadows et al. |
| 6,393,325 B1 | 5/2002 | Mann et al. |
| 6,393,328 B1 | 5/2002 | McGraw et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,438,423 B1 | 8/2002 | Rezai et al. |
| 6,440,090 B1 | 8/2002 | Schallhorn |
| 6,473,644 B1 | 10/2002 | Terry, Jr. et al. |
| 6,487,446 B1 | 11/2002 | Hill et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,587,727 B2 | 7/2003 | Osorio et al. |
| 6,600,954 B2 | 7/2003 | Cohen et al. |
| 6,609,030 B1 | 8/2003 | Rezai et al. |
| 6,609,031 B1 | 8/2003 | Law et al. |
| 6,610,713 B2 | 8/2003 | Tracey |
| 6,622,047 B2 | 9/2003 | Barrett et al. |
| 6,622,048 B1 | 9/2003 | Mann |
| 6,659,968 B1 | 12/2003 | McClure |
| 6,662,051 B1 | 12/2003 | Eraker et al. |
| 6,671,556 B2 | 12/2003 | Osorio et al. |
| 6,675,046 B2 | 1/2004 | Holsheimer |
| 6,684,105 B2 | 1/2004 | Cohen et al. |
| 6,712,753 B2 | 3/2004 | Manne |
| 6,714,822 B2 | 3/2004 | King et al. |
| 6,721,603 B2 | 4/2004 | Zabara et al. |
| 6,754,539 B1 | 6/2004 | Erickson |
| 6,761,715 B2 | 7/2004 | Carroll et al. |
| 6,795,737 B2 | 9/2004 | Gielen et al. |
| 6,856,315 B2 | 2/2005 | Eberlein |
| 6,871,090 B1 | 3/2005 | He et al. |
| 6,871,099 B1 | 3/2005 | Whitehurst et al. |
| 6,885,888 B2 | 4/2005 | Rezai |
| 6,892,097 B2 | 5/2005 | Holsheimer |
| 6,895,280 B2 | 5/2005 | Meadows et al. |
| 6,907,295 B2 | 6/2005 | Gross et al. |
| 6,920,357 B2 | 7/2005 | Osorio et al. |
| 6,923,784 B2 | 8/2005 | Stein |
| 6,928,320 B2 | 8/2005 | King |
| 6,941,173 B2 | 9/2005 | Nachum |
| 6,950,707 B2 | 9/2005 | Whitehurst |
| 6,961,618 B2 | 11/2005 | Osorio et al. |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,024,247 B2 | 4/2006 | Gliner et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,158,826 B1 | 1/2007 | Kroll et al. |
| 7,162,303 B2 | 1/2007 | Levin et al. |
| 7,162,304 B1 | 1/2007 | Bradley |
| 7,167,750 B2 | 1/2007 | Knudson et al. |
| 7,174,215 B2 | 2/2007 | Bradley |
| 7,177,690 B2 | 2/2007 | Woods et al. |
| 7,177,691 B2 | 2/2007 | Meadows et al. |
| 7,177,702 B2 | 2/2007 | Wallace et al. |
| 7,180,760 B2 | 2/2007 | Varrichio et al. |
| 7,181,289 B2 | 2/2007 | Pflueger et al. |

(56) References Cited

U.S. PATENT DOCUMENTS

| | | | |
|---|---|---|---|
| 7,206,640 B1 * | 4/2007 | Overstreet | A61N 1/36036 607/57 |
| 7,212,865 B2 | 5/2007 | Cory | |
| 7,225,016 B1 | 5/2007 | Koh | |
| 7,225,035 B2 | 5/2007 | Brabec et al. | |
| 7,231,254 B2 | 6/2007 | DiLorenzo | |
| 7,236,822 B2 | 6/2007 | Dobak, III | |
| 7,239,912 B2 | 7/2007 | Dobak, III | |
| 7,242,984 B2 | 7/2007 | DiLorenzo | |
| 7,252,090 B2 | 8/2007 | Goetz | |
| 7,260,436 B2 | 8/2007 | Kilgore et al. | |
| 7,266,412 B2 | 9/2007 | Stypulkowski | |
| 7,276,057 B2 | 10/2007 | Gerber | |
| 7,288,062 B2 | 10/2007 | Spiegel | |
| 7,313,440 B2 | 12/2007 | Miesel | |
| 7,324,852 B2 | 1/2008 | Barolat et al. | |
| 7,326,181 B2 | 2/2008 | Katims | |
| 7,333,857 B2 | 2/2008 | Campbell | |
| 7,337,005 B2 | 2/2008 | Kim et al. | |
| 7,337,006 B2 | 2/2008 | Kim et al. | |
| 7,346,398 B2 | 3/2008 | Gross et al. | |
| 7,349,743 B2 | 3/2008 | Tadlock | |
| RE40,279 E | 4/2008 | Sluijter et al. | |
| 7,359,751 B1 | 4/2008 | Erickson et al. | |
| 7,363,076 B2 | 4/2008 | Yun et al. | |
| 7,386,341 B2 | 6/2008 | Hafer et al. | |
| 7,389,145 B2 | 6/2008 | Kilgore et al. | |
| 7,393,351 B2 | 7/2008 | Woloszko et al. | |
| 7,433,734 B2 | 10/2008 | King | |
| 7,444,183 B2 | 10/2008 | Knudson et al. | |
| 7,447,546 B2 | 11/2008 | Kim et al. | |
| 7,450,993 B2 | 11/2008 | Kim et al. | |
| 7,463,927 B1 | 12/2008 | Chaouat | |
| 7,483,747 B2 | 1/2009 | Gliner | |
| 7,489,969 B2 | 2/2009 | Knudson et al. | |
| 7,493,172 B2 | 2/2009 | Whitehurst et al. | |
| 7,496,404 B2 | 2/2009 | Meadows et al. | |
| 7,502,651 B2 | 3/2009 | Kim et al. | |
| 7,502,652 B2 | 3/2009 | Gaunt et al. | |
| 7,571,007 B2 | 8/2009 | Erickson et al. | |
| 7,580,753 B2 | 8/2009 | Kim et al. | |
| 7,599,737 B2 | 10/2009 | Yomtov et al. | |
| 7,613,520 B2 | 11/2009 | De Ridder | |
| 7,634,317 B2 | 12/2009 | Ben-David et al. | |
| 7,676,269 B2 | 3/2010 | Yun et al. | |
| 7,689,289 B2 | 3/2010 | King | |
| 7,734,340 B2 | 6/2010 | De Ridder | |
| 7,742,810 B2 | 6/2010 | Moffitt et al. | |
| 7,761,168 B2 | 7/2010 | Gross | |
| 7,761,170 B2 | 7/2010 | Kaplan et al. | |
| 7,778,704 B2 | 8/2010 | Rezai | |
| 7,813,803 B2 | 10/2010 | Heruth et al. | |
| 7,826,901 B2 | 11/2010 | Lee et al. | |
| 7,844,338 B2 | 11/2010 | Knudson et al. | |
| 7,853,322 B2 | 12/2010 | Bourget et al. | |
| 7,860,570 B2 | 12/2010 | Whitehurst et al. | |
| 7,877,136 B1 | 1/2011 | Moffitt et al. | |
| 7,877,146 B2 | 1/2011 | Rezai | |
| 7,890,166 B2 | 2/2011 | Heruth et al. | |
| 7,890,176 B2 | 2/2011 | Jaax et al. | |
| 7,890,182 B2 | 2/2011 | Parramon et al. | |
| 7,914,452 B2 | 3/2011 | Hartley et al. | |
| 7,933,654 B2 | 4/2011 | Merfeld et al. | |
| 7,937,145 B2 | 5/2011 | Dobak | |
| 8,010,198 B2 | 8/2011 | Libbus et al. | |
| 8,027,718 B2 | 9/2011 | Spinner et al. | |
| 8,046,075 B2 | 10/2011 | Rezai | |
| 8,060,208 B2 | 11/2011 | Kilgore et al. | |
| 8,075,556 B2 | 12/2011 | Betts | |
| 8,082,039 B2 | 12/2011 | Kim et al. | |
| 8,209,028 B2 | 6/2012 | Skelton et al. | |
| 8,224,453 B2 | 7/2012 | De Ridder | |
| 8,224,459 B1 | 7/2012 | Pianca et al. | |
| 8,255,057 B2 | 8/2012 | Walker et al. | |
| 8,280,515 B2 | 10/2012 | Greenspan | |
| 8,340,775 B1 | 12/2012 | Cullen et al. | |
| 8,355,792 B2 | 1/2013 | Alataris et al. | |
| 8,359,102 B2 | 1/2013 | Alataris et al. | |
| 8,359,103 B2 | 1/2013 | Alataris et al. | |
| 8,364,271 B2 | 1/2013 | De Ridder | |
| 8,364,273 B2 | 1/2013 | De Ridder | |
| 8,428,735 B2 | 4/2013 | Littlewood et al. | |
| 8,509,906 B2 | 8/2013 | Walker et al. | |
| 8,612,018 B2 | 12/2013 | Gillbe | |
| 8,649,874 B2 | 2/2014 | Alataris et al. | |
| 8,666,506 B2 | 3/2014 | King | |
| 8,718,781 B2 | 5/2014 | Alataris | |
| 8,849,410 B2 | 9/2014 | Walker et al. | |
| 8,886,326 B2 | 11/2014 | Alataris et al. | |
| 8,886,328 B2 | 11/2014 | Alataris et al. | |
| 8,892,209 B2 | 11/2014 | Alataris et al. | |
| 8,918,172 B2 | 12/2014 | Moffitt et al. | |
| 8,918,190 B2 | 12/2014 | Libbus et al. | |
| 9,002,459 B2 | 4/2015 | Lee et al. | |
| 9,067,076 B2 | 6/2015 | Nolan et al. | |
| 9,180,298 B2 | 11/2015 | Alataris et al. | |
| 9,295,840 B1 | 3/2016 | Thacker | |
| 9,327,127 B2 | 5/2016 | Alataris et al. | |
| 9,561,370 B2 | 2/2017 | Rezai | |
| 9,895,539 B1 | 2/2018 | Heit et al. | |
| 2002/0055779 A1 | 5/2002 | Andrews | |
| 2002/0128700 A1 | 9/2002 | Cross | |
| 2003/0100931 A1 | 5/2003 | Mullett | |
| 2003/0120323 A1 | 6/2003 | Meadows et al. | |
| 2003/0125786 A1 | 7/2003 | Gliner et al. | |
| 2004/0015202 A1 | 1/2004 | Chandler et al. | |
| 2004/0034394 A1 | 2/2004 | Woods et al. | |
| 2004/0039425 A1 | 2/2004 | Greenwood-Van Meerveld | |
| 2004/0059395 A1 | 3/2004 | North et al. | |
| 2004/0073273 A1 | 4/2004 | Gluckman et al. | |
| 2004/0093093 A1 | 5/2004 | Andrews | |
| 2004/0116977 A1 | 6/2004 | Finch et al. | |
| 2004/0122477 A1 | 6/2004 | Whitehorse | |
| 2004/0127953 A1 | 7/2004 | Kilgore et al. | |
| 2004/0162590 A1 | 8/2004 | Whitehurst et al. | |
| 2004/0162594 A1 | 8/2004 | King et al. | |
| 2004/0167584 A1 | 8/2004 | Carroll et al. | |
| 2004/0172085 A1 | 9/2004 | Knudson et al. | |
| 2004/0176812 A1 | 9/2004 | Knudson et al. | |
| 2004/0186532 A1 | 9/2004 | Tadlock | |
| 2004/0193228 A1 | 9/2004 | Gerber | |
| 2004/0210270 A1 | 10/2004 | Erickson | |
| 2004/0210271 A1 | 10/2004 | Campen et al. | |
| 2004/0267330 A1 | 12/2004 | Lee et al. | |
| 2005/0021104 A1 | 1/2005 | DiLorenzo | |
| 2005/0033381 A1 | 2/2005 | Carter et al. | |
| 2005/0038489 A1 | 2/2005 | Grill | |
| 2005/0060001 A1 | 3/2005 | Singhal et al. | |
| 2005/0070982 A1 | 3/2005 | Heruth et al. | |
| 2005/0113877 A1 | 5/2005 | Spinelli et al. | |
| 2005/0113878 A1 | 5/2005 | Gerber | |
| 2005/0113882 A1 | 5/2005 | Cameron et al. | |
| 2005/0119713 A1 | 6/2005 | Whitehurst et al. | |
| 2005/0143789 A1 | 6/2005 | Whitehurst et al. | |
| 2005/0149148 A1 | 7/2005 | King | |
| 2005/0153885 A1 | 7/2005 | Yun et al. | |
| 2005/0154435 A1 | 7/2005 | Stern et al. | |
| 2005/0182453 A1 | 8/2005 | Whitehurst et al. | |
| 2005/0240241 A1 | 10/2005 | Yun et al. | |
| 2005/0245978 A1 | 11/2005 | Varrichio et al. | |
| 2005/0246006 A1 | 11/2005 | Daniels | |
| 2005/0267545 A1 | 12/2005 | Cory | |
| 2005/0278000 A1 | 12/2005 | Strother et al. | |
| 2006/0004422 A1 | 1/2006 | De Ridder | |
| 2006/0009820 A1 | 1/2006 | Royle | |
| 2006/0015153 A1 | 1/2006 | Gliner et al. | |
| 2006/0025832 A1 | 2/2006 | O'Keeffe et al. | |
| 2006/0030895 A1 | 2/2006 | Simon et al. | |
| 2006/0030899 A1 | 2/2006 | O'Keeffe et al. | |
| 2006/0041285 A1 | 2/2006 | Johnson | |
| 2006/0052836 A1 | 3/2006 | Kim et al. | |
| 2006/0074456 A1 | 4/2006 | Pyles et al. | |
| 2006/0079936 A1 | 4/2006 | Boveja et al. | |
| 2006/0079937 A1 | 4/2006 | King et al. | |

(56) References Cited

U.S. PATENT DOCUMENTS

| | | |
|---|---|---|
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167525 A1 | 7/2006 | King |
| 2006/0168805 A1 | 8/2006 | Hegland et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2007/0021801 A1 | 1/2007 | Heruth et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0106337 A1 | 5/2007 | Errico et al. |
| 2007/0106342 A1 | 5/2007 | Schumann |
| 2007/0142863 A1 | 6/2007 | Bradley |
| 2007/0142874 A1 | 6/2007 | John |
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0203537 A1 | 8/2007 | Goetz et al. |
| 2007/0213789 A1 | 9/2007 | Nolan et al. |
| 2007/0233192 A1 | 10/2007 | Craig |
| 2007/0233194 A1 | 10/2007 | Craig |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265681 A1 | 11/2007 | Gerber et al. |
| 2007/0293915 A1 | 12/2007 | Kilgore et al. |
| 2007/0299482 A1 | 12/2007 | Littlewood et al. |
| 2008/0033511 A1 | 2/2008 | Dobak |
| 2008/0045775 A1 | 2/2008 | Lozano et al. |
| 2008/0058878 A1 | 3/2008 | King |
| 2008/0058888 A1 | 3/2008 | King |
| 2008/0097539 A1 | 4/2008 | Belalcazar |
| 2008/0103570 A1 | 5/2008 | Gerber |
| 2008/0109045 A1 | 5/2008 | Gross et al. |
| 2008/0154333 A1 | 6/2008 | Knudson et al. |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2008/0319511 A1* | 12/2008 | Pless .................. A61B 5/0031 607/59 |
| 2009/0018617 A1 | 1/2009 | Skelton et al. |
| 2009/0024187 A1 | 1/2009 | Erickson et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0112282 A1 | 4/2009 | Kast et al. |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0241190 A1 | 9/2010 | Kilgore et al. |
| 2010/0256696 A1 | 10/2010 | Schleicher et al. |
| 2010/0262205 A1 | 10/2010 | De Ridder |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0089200 A1 | 4/2012 | Ranu et al. |
| 2012/0150252 A1 | 6/2012 | Feldman et al. |
| 2012/0158093 A1 | 6/2012 | Alataris et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0066411 A1 | 3/2013 | Thacker et al. |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0261695 A1 | 10/2013 | Thacker et al. |
| 2013/0261696 A1 | 10/2013 | Thacker et al. |
| 2013/0261697 A1 | 10/2013 | Parker |
| 2014/0031896 A1 | 1/2014 | Alataris et al. |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032182 A1 | 1/2015 | Alataris et al. |
| 2015/0032183 A1 | 1/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |

(56) References Cited

U.S. PATENT DOCUMENTS

| | | |
|---|---|---|
| 2015/0217116 A1 | 8/2015 | Parramon et al. |
| 2015/0343220 A1 | 12/2015 | Alataris et al. |
| 2016/0121119 A1 | 5/2016 | Alataris et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0375254 A1 | 12/2016 | Walker et al. |
| 2017/0050021 A1 | 2/2017 | Cosman, Sr. |
| 2017/0165485 A1 | 6/2017 | Sullivan et al. |

FOREIGN PATENT DOCUMENTS

| | | |
|---|---|---|
| EP | 2243511 A2 | 10/2010 |
| EP | 2448633 A1 | 5/2012 |
| EP | 2630984 A1 | 8/2013 |
| GB | 2449546 A | 11/2008 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-2003011361 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006057734 A1 | 6/2006 |
| WO | WO-2006063458 | 6/2006 |
| WO | WO-2006083884 A1 | 8/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-2009097226 | 8/2009 |
| WO | WO-20090129329 A1 | 10/2009 |
| WO | WO-2010111358 A2 | 9/2010 |
| WO | WO-2011014570 A1 | 2/2011 |
| WO | WO-2016154091 A1 | 9/2016 |

OTHER PUBLICATIONS

"The Need for Mechanism-Based Medicine in Neuromodulation," Neuromodulation: Technology at the Neural Interface, 2012, 7 pages.
Acticare.com website, http://web.archive.org/web/*/acticare.com, Internet Archive Way Back Machine, 2012, 22 pages.
Advanced Neuromodulation Systems, Compustim SCS Systems, Clinical Manual, 1997, 52 pages.
Agnew et al., "Considerations for safety with chronically implanted nerve electrodes," Epilepsia, 31.s2, 1990, 6 pages.
Al-Kaisy et al., "10 kHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.
Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.
Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural, Interface, 2015, 6 pages.
Al-Kaisy et al., Poster: "High-Frequency Spinal Cord Stimulation at 10 kHz for the Treatment of Chronic Back Pain Patients without Prior Back Surgery," 1 page.
Alo et al., "New Trends in Neuromodulation for the Management of Neuropathic Pain," Neurosurgery, vol. 50, No. 4, Apr. 2002, 15 pages.
Augustinsson et al., "Spinal Cord Stimulation in Cardiovascular Disease," Functional Neurosurgery, vol. 6, No. 1, Jan. 1995, 10 pages.
Bara et al., Poster re: High Frequency Spinal Cord Stimulation for Dominant Back Pain—1 year follow up, 2013, 1 page.
Barolat et al., "Multifactorial Analysis of Epidural Spinal Cord Stimulation," Stereotactic and Functional Neurosurgery, 1991; 56: 77-103.
Barolat et al., "Spinal Cord Stimulation for Chronic Pain Management," Seminars in Neurosurgery, vol. 15, Nos. 2/3, 2004, 26 pages.
Barolat et al., "Surgical Management of Pain—Spinal Cord Stimulation: Equipment and Implantation Techniques," Chapter 41, Thieme Medical Publishers, New York, 2002, 11 pages.
Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.
Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.
Bhadra et al., "High Frequency electrical conduction block of the pudendal nerve," Journal of Neural Engineering—Institute of Physics Publishing, 2006, 8 pages.
Bhadra et al., Stimulation of High-Frequency Sinusoidal Electrical Block of Mammalian Myelinated Axons, J Comput Neurosci, 22:313-326, 2007.
Bhadra MD, Niloy et al., "High-Frequency Electrical Conduction Block of Mammalian Peripheral Motor Nerve," Muscle and Nerve, Dec. 2005, 9 pages.
BionicNAVIGATOR Software Guide, Part MP9055261-001, 2004, 58 pages.
Boger et al., "Bladder Voiding by Combined High Frequency Electrical Pudendal Nerve Block and Sacral Root Stimulation," Neurology and Urodynamics, 27, 2008, 5 pages.
Boston Scientific "Precision™ Spinal Cord Stimulator System Clinician Manual—Directions for Use," 2015, 74 pages.
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Bowman and McNeal, Response of Single Alpha Motoneurons to High-Frequency Pulse Trains, Appl. Neurophysiol. 49, p. 121-138, 1986, 10 pages.
Braun Medical Inc. http:www.braunusa.com/stimuplex/index.html, p. 2.
Broseta et al., "High-Frequency cervical spinal cord stimulation in spasticity and motor disorders," Advances in Stereotactic and Functional Neurosurgery 7. Springer Verlag 1987, 6 pages.
Burton, Charles, "Dorsal Column Stimulation: Optimization of Application," Surgical Neurology, vol. 4, No. 1, Jul. 1975, 10 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Survival During Exposure to Pulsed and Continuous Radiofrequency Energy," Journal of Pain, vol. 4, No. 4, May 2003, 6 pages.

(56) References Cited

OTHER PUBLICATIONS

Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
Capdevila et al., "Continuous Peripheral Nerve Blocks in Hospital Wards after Orthopedics Surgery," Anesthesiology 2005, 103:1035-45, 10 pages.
ClinicalTrials.gov, "Safety and Effectiveness Study of the Precision SCS System Adapted for High-Rate Spinal Cord Stimulation (Accelerate)," https://clinicaltrials.gov/ct2/show/NCT02093793?term=boston+scientific&recr=Open&cond=%22Pain%22&rank=3, Feb. 2015, 3 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.
Cuellar et al., "Effect of High Frequency Alternating Current on Spinal Afferent Nociceptive Transmission," Neuromodulation: Technology at the Neural Interface, 2012, 10 pages.
Dapoigny, "Vagal influence on colonic motor activity in conscious nonhuman primates," AM Journal Physilogical Society, 1992, 6 pages.
De Carolis et al., Poster: "Efficacy of Spinal Cord Stimulation (SCS) in the Treatment of Failed Back Surgery Syndrome (FBSS): a comparative study," 2013, 1 page.
De Ridder et al., U.S. Appl. No. 60/895,061, Applicant: Dirk De Ridder, filed Mar. 15, 2007, 47 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
European Extended Search Report for European Patent Application No. 14193327, Applicant: Nevro Corporation, dated May 28, 2015, 7 pages.
European Extended Search Report for European Patent Application No. 17152808, Applicant: Nevro Corporation, dated May 12, 2017, 7 pages.
Faccenda et al., "Complications of Regional Anesthesia Incidence and Prevention, Drug Safety: An International Journal of Medical Toxicology and Drug Experience" Adis International Limited, 2001: 24(6), 30 pages.
Feeling vs. Function Poster, Mager and Associates Consulting, 2009, 1 page.
Gainer et al., "Use of the Peripheral Nerve Stimulator and Standard, Unsheathed Needles in Performing Regional Nerve Blocks," CRMA: The Clinical Forum for Nurse Anesthetists, vol. 3, No. 4, Nov. 1992, 4 pages.
Geddes, "A Short History of the electrical stimulation of excitable tissue—Including Electrotherapeutic Applications," The Physiologist, vol. 27, No. 1, Feb. 1984, 51 pages.
Grill, Warren et al., "Stimulus Waveforms for Selective Neural Stimulation," IEEE Engineering in Medicine and Biology, Jul./Aug. 1995, pp. 375-385.
Gulve et al., Poster: "10kHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
House et al., "Safety and Efficacy of the House/3M Cochlear Implant in Profoundly Deaf Adults," Otolaryngologic Clinics of North America, vol. 19, No. 2, May 1986, 12 pages.
Huxely et al., "Excitation and Conduction in Nerve: Quantitative Analysis," Science, Sep. 11, 1964; 145: 1154-9.
International Neuromodulation Society 10th World Congress, Neuromodulation: Technology that Improves Patient Care, London, England, May 21-26, 2011, 385 pages.
International Search Report and Written Opinion, International Application No. PCT/US2010/022442, Applicant: Nevro Corporation, European Patent Office, dated Apr. 14, 2010, 17 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
Jezernik et al., "Electrical Stimulation for the Treatment of Bladder Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.
Kapural et al., "Comparison of 10-kHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord

(56) References Cited

OTHER PUBLICATIONS

Stimulation for Treatment of Chronic Back and Leg Pain," Anesthesiology the Journal of American Society of Anesthesiologists, Inc., 2015, 11 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Klein, "Continuous Peripheral Nerve Blocks," Anesthesiology, vol. 103, pp. 921-1044, Nov. 2005.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 kHz Spinal Cord Stimulation in Chronic Refractory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. 1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
Mediati, R.D., "Mechanisms of Spinal Cord Stimulation," Florence, Oct. 2, 2002, 31 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The MED-EL SONATATI 100 Cochlear Implant: An evaluation of its safety in adults and children," Acta Oto-Laryngologica, vol. 131, No. 5, 2011, 8 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," Pain 80, 1999, 3 pages.
Nashold et al., "Dorsal Column Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx, 2016, 3 pages.
Nevro—Clinical Evidence www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview, www.nevro.com/English/Physicians/Physician-Overview/default.aspx, 2016, 5 pages.
Nevro—Senza System, http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro's presentation of HF10 therapy on Nevro's website, http://www.nevro.com/English/Home/default.aspx, 2016, 2 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pp./coch.aspx, Jun. 29, 2012, 2 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.

(56) References Cited

OTHER PUBLICATIONS

North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
North et al., "Spinal Cord Stimulation With Interleaved Pulses: A Randomized, Controlled Trial," vol. 10, No. 4, 2007, 9 pages.
Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.
Oakley et al., "Spinal Cord Stimulation in Axial Low Back Pain: Solving the Dilemma," Pain Medicine, vol. 7, No. S1, 2006, 6 pages.
Oakley, John C., "Spinal Cord Stimulation Mechanisms of Action," SPINE vol. 27, No. 22 copyright 2002, 10 pages.
OHSIPP Summer Newsletter, The Official Newsletter for the Ohio Society of Interventional Pain Physicians, vol. 1 Ed. 2, Summer 2010, 8 pages.
Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.
Palmer et al., "Transcutaneous electrical nerve stimulation and ; transcutaneous spinal electroanalgesia: A preliminary efficacy and mechanisms-based investigation," Physiotherapy, 95, 2009, 7 pages.
Paterson CA et al., "Determinants of Occurrence and Volume f Transpyloric Flow During Gastric Emptying of Liquids in Dogs: Importance of Vagal Input," Digital Disease and Science, vol. 45, No. 8, Aug. 2000,8 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, May 14, 2015, 45 pages.
Petrofsky et al. "Impact of Recruitment Order on Electrode Design for Neural Prosthetics of Skeletal Muscle," Am Journal of Physical Medicine, 1981, vol. 60, No. 5, pp. 243-253.
Prausnitz et al., "The Effects of Electric Current Applied to Skin: A Review for Transdermal Drug Delivery," Advanced Drug Delivery Reviews 18, ; 1996, 31 pages.
Precision—Physician System Handbook, Advanced Bionic Corporation, Part 9055253-0001, 2005, 92 pages.
Precision—Physician Trail Kit Insert, Advanced Bionic Corporation, Part 9055258-0001, 2005, 2 pages.
Precision Spinal Cord Stimulation—Charging System Insert, Advanced Bionic Corporation, Part 9055074-0001, 2004, 2 pages.
Precision Spinal Cord Stimulation—Charging System, Advanced Bionic Corporation, Part 9055259-0001, 2004, 2 pages.
Precision Spinal Cord Stimulation—Patient System Handbook, Advanced Bionic Corporation, Part 9055072-0001, 2004, 93 pages.
Precision Spinal Cord Stimulation—Patient Trial Journal, Advanced Bionic Corporation, Part 9055260-0001, 2004, 10 pages.
Precision Spinal Cord Stimulation—Physician Implant Manual, Advanced Bionic Corporation, Part 9055100, 2004, 62 pages.
Precision Spinal Cord Stimulation—Physician Implant Manual, Advanced Bionic Corporation, Part 9055255-0001, 2005, 70 pages.
Precision Spinal Cord Stimulation—Physician Lead Manual, Advanced Bionic Corporation, Part No. 9055183-001, May 2004, 31 pages.
Precision Spinal Cord Stimulation—Physician Lead Manual, Advanced Bionic Corporation, Part 9055095, 2004, 62 pages.
Precision Spinal Cord Stimulation—Physician Lead Manual, Advanced Bionic Corporation, Part 9055256-0001, 2005, 56 pages.
Precision Spinal Cord Stimulation—Physician Trail Handbook, Advanced Bionic Corporation, Part 9055254-0001, 2005, 66 pages.
Precision Spinal Cord Stimulation—Physician Trail Kit Model SC-7005, Part 9055066-001, Advanced Bionic Corporation, 2004, 2 pages.
Precision Spinal Cord Stimulation—Remote Control Model SC-5200, Part 9055107-001, 2004, Advanced Bionic Corporation, 2 pages.
Precision Spinal Cord Stimulation—Remote Control Model SC-5210, Advanced Bionic Corporation, Part 9055257-001, 2005, 2 pages.
Precision Spinal Cord Stimulation System—Patient System Handbook, Advanced Bionic Corporation, Part No. 9055184-001, May 2004, 86 pages.
Precision Spinal Cord Stimulation System, Patient Trial Handbook, Part 9055078, 2004, 74 pages.
Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.
Pudenz et al., "Neural Stimulation: Clinical and Laboratory Experiences", Surg. Neurol, 39:235-242 (1993).
Rapcan et al., Clinical Study, "High-Frequency—Spinal Cord Stimulation," Indexed and Abstracted in Science Citation Index Expanded and in Journal Citation Reports, 2015, 3 pages.
Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.
Remedi Pain Relief—ENM (Electronic Nerve Modulation), https://web.archive.org/web/20050906181041/http://www.remediuk.com/trials.htm, 2005, 5 pages.
Resume of Jason D. Rahn, Jan. 7, 2015, 2 pages.
Robb et al., "Transcutaneous Electrical Nerve Stimulation vs. Transcutaneous Spinal Electroanalgesia for Chronic Pain Associated with ; Breast Cancer Treatments," Journal of Pain and Symptom Management, vol. 33, No. 4, Apr. 2007, 10 pages.
Royle, John., "Transcutaneous Spinal Electroanalgesia and Chronic Pain," Physiotherapy, vol. 86, No. 5, May 2000, 1 page.
Schulman et al., "Battery Powered BION FES Network," Proceedings of the 26th Annual Conference of the IEEE EMBS, San Francisco, CA., Sep. 1-5, 2004, 4 pages.
Science Daily, "Chronic Pain Costs U.S. up to $635 billion, study shows," www.sciencedaily.com/releases/2012/09/120911091100.htm, Sep. 11, 2012, 2 pages.
Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.
Sharan et al., "Evolving Patterns of Spinal Cord Stimulation in Patients Implanted for Intractable Low Back and Leg Pain," International Neuromodulation Society, vol. 5, No. 3, 2002, 13 pages.
Shealy et al., "Dorsal Column Electrohypalgesia," Jul. 1969, 8 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967,3 pages.
Shelden et al., "Depolarization in the Treatment of Trigeminal Neuralgia," Evaluation of Compression and Electrical Methods, Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 6 pages.
Shelden et al., "Electrical stimulation of the nervous system," Surg. Neurol. vol. 4, No. 1, Jul. 1975, 6 pages.
Simpson et al., "A Randomized, Double-Blind, Crossover Study of the Use of Transcutaneous Spinal Electroanalgesia in Patients with Pain from ; Chronic Critical Limb lschemia," Journal of Pain and Symptom Management, vol. 28, No. 5, Nov. 2004, 6 pages.

(56) References Cited

OTHER PUBLICATIONS

Simpson, BA, "Spinal Cord Stimulation in 60 cases of Intractable Pain." Journal of Neurology, Neurosurgery and Psychiatry, 1991; 54 pp. 196-199.

Simpson, BA, "Spinal Cord Stimulation." British Journal of Neurosurgery, Feb. 11, 1997, (1), 5-11, 7 pages.

Sluijter et al., "The Effects of Pulsed Radiofrequency Fields Applied to the Dorsal Root Ganglion—A Preliminary Report," The Pain Clinic, vol. 11, No. 2, 1998, 12 pages.

Smet et al, "Successful Treatment of Low Back Pain with a Novel Neuromodulation Device," AZ Nikolaas, 12 pages.

Smet et al., Poster: "High-Frequency Spinal Cord Stimulation at 10 kHz after Failed Traditional Spinal Cord Stimulation," NANS, 2013, 1 page.

Solomonow et al., "Control of Muscle Contractile Force through Indirect High-Frequency Stimulation," AM Journal of Physical Medicine, 1983, vol. 62, No. 3, pp. 71-82.

St. Jude Medical, "Eon Mini™ Rechargeable IPG," Apr. 29, 2013, 3 pages.

St. Jude Medical, "Individualized Therapy through Diverse Lead Options," 2008, 6 pages.

Stimwave, News Release: "Stimwave Receives FDA Approval for High Frequency IDE," http://stimwave.com/newsroom/latest-news, Jun. 9, 2015, 2 pages.

Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.

Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.

Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.

Tan et al., "Intensity Modulation: A Novel Approach to Percept Control in Spinal Cord Stimulation," Neuromodulation Technology at the Neural Interface, International Neuromodulation Society 2015, 6 pages.

Tanner, J.A., "Reversible blocking of nerve conduction by alternating-current excitation," Nature, Aug. 18, 1962; 195: 712-3.

Taylor et al., "The Cross Effectiveness of Spinal Cord Stimulation in the Treatment of Pain: A Systematic Review of the Literature," Journal of Pain and Symptom Management, vol. 27, No. 4., Apr. 2001, 9 pages.

Tesfaye et al., "Electrical Spinal Cord Stimulation for Painful Diabetic Peripheral Neuropathy," The Lancet, vol. 348, Dec. 21-28, 1996, 4 pages.

Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.

Tiede et al., "Novel Spinal Cord Stimulation Parameters in Patients with Predominate Back Pain," Neuromodulation: Technology at the Neural Interface, 2013, 6 pages.

Tollison et al., "Practical Pain Management; Neurostimulation Techniques," Chapter 12, Lippincott Williams and Wilkins, Third Edition, 2002, 13 pages.

Towell et al., "High Frequency non-invasive stimulation over the spine: Effects on mood and mechanical pain tolerance in normal subjects," Behavioral Neurology, vol. 10, 1997, 6 pages.

Urban et al., "Percutaneous epidural stimulation of the spinal cord for relief of pain—Long Term Results," Journal of Neurosurgery, vol. 48, Mar. 1978, 7 pages.

Vadalouca et al., "Therapeutic Management of Chronic Neuropathic Pain: An Examination of Pharmacologic Treatment," Annals New York Academy of Sciences, 2006, pp. 164-186.

Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.

Van Buyten et al., "Pain Relief for Axial Back Pain Patients," INS Meeting Poster, 1 page.

Van Den Honert et al. "Generation of Unidirectionally Propagated Action Potentials Nerve by Brief Stimuli" Science, vol. 26, pp. 1311-1312.

Van Den Honert, Mortimer JT, "A Technique for Collison Block of Peripheral Nerve: Frequency Dependence," MP-11 IEEE Trans. Biomed, Eng. 28: 379-382, 1981.

Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neuromodulation Society, 2014, 4 pages.

Verrills et al., "Peripheral Nerve Field Stimulation for Chronic Pain: 100 Cases and Review of the Literature," Pain Medicine, 2011, 11 pages.

Verrills et al., "Salvaging Failed Neuromodulation Implants with Nevro High Frequency Spinal Cord System," NANS Poster, 2013, 1 page.

Von Korff et al., "Assessing Global Pain Severity by Self-Report in Clinical and Health Services Research," SPINE, vol. 25, No. 24, 2000, 12 pages.

Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.

Ward et al., "Electrical Stimulation Using Kilohertz-Frequency Alternating Current," Journal of the American Physical Therapy Association, vol. 89, No. 2, Feb. 2009, 12 pages.

Ward et al., "Variation in Motor Threshold with Frequency Using kHz Frequency Alternating Current," Muscle and Nerve, Oct. 2001, 9 pages.

Webster's Third New International Dictionary of the English Language Unabridged, "Paresthesia," 1993, 3 pages.

Weinberg et al., "Increasing the oscillation frequency of strong magnetic fields above 101 kHz significantly raises peripheral nerve excitation thresholds," Medical Physics Letter, May 2012, 6 pages.

Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

Woo MY, Campbell B. "Asynchronous Firing and Block of Peripheral Nerve Conduction by 20KC Alternating Current," Los Angeles Neuro Society, Jun. 1964; 87-94, 5 pages.

Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood et al., "Pulse Width Programming in Spinal Cord Stimulation: A Clinical Study," Pain Physician Journal, Jul./Aug. 2010, 16 pages.

Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.

Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.

Zhang et al., Changes Across Time in Spike Rate and Spike Amplitude of Auditory Nerve Fibers Stimulated by Electric Pulse Trains, Journal of the Association for Research of Otolaryngology, 2007, 17 pages.

Abejon et al., "Is Impedance a Parameter to be Taken into Account in Spinal Cord Stimulation?" Pain Physician, 2007, 8 pages.

Al-Kaisy et al., "Prospective, Randomized, Sham-Control, Double Blind, Crossover Trial of Subthreshold Spinal Cord Stimulation at

(56) References Cited

OTHER PUBLICATIONS

Various Kilohertz Frequencies in Subjects Suffering from Failed Back Surgery Syndrome," International Neuromodulation Society, 2018, 9 pages.

Alo et al., "Factors Affecting Impedance of Percutaneous Leads in Spinal Cord Stimulation," International Neuromodulation Society, vol. 9, No. 2, 2006, 8 pages.

Bronstein et al., "The Rationale Driving the Evolution of Deep Brain Stimulation of Constant-Current Devices," International Neuromodulation Society 2014, 5 pages.

McCreery et al., "Charge Density and Charge Per Phase as Cofactors in Neural Injury Induced by Electrical Stimulation," IEEE Transactions on Biomedical Engineering, vol. 37, No. 10, Oct. 1990, 6 pages.

McCreery et al., "Damage in Peripheral Nerve from Continuous Electrical Stimulation: Comparison of Two Stimulus Waveforms," Medical and Biological Engineering and Computing, Jan. 1992, 6 pages.

McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.

Nevro—Leadership Through Innovation, J. P. Morgan 36th Annual Healthcare Conference, Jan. 8, 2018, 21 pages.

Renew Neurostimulation System—Clinician's Manual—Advanced Neuromodulation Systems, Life Gets Better, 2000, 77 pages.

Rosenblueth et al., "The Blocking and Deblocking Effects of Alternating Currents on Nerve," Department of Physiology in Harvard Medical School, Nov. 1938, 13 pages.

St. Jude Medical, "Clinician's Manual—Percutaneous Lead Kit, Models 3143, 3146, 3149, 3153, 3156, 3159, 3183, 3186, 3189," 2016, 24 pages.

Wesselink et al., Analysis of Current Density and Related Parameters in Spinal Cord Stimulation, IEEE Transaction on Rehabilitation Engineering vol. 6, No. 2, Jun. 1998, 8 pages.

\* cited by examiner

SYSTEMS AND METHODS FOR PRODUCING ASYNCHRONOUS NEURAL RESPONSES TO TREAT PAIN AND/OR OTHER PATIENT CONDITIONS

CROSS-REFERENCE TO RELATED APPLICATIONS

This is a continuation application of U.S. patent application Ser. No. 15/192,914, filed Jun. 24, 2016, entitled SYSTEMS AND METHODS FOR PRODUCING ASYNCHRONOUS NEURAL RESPONSES TO TREAT PAIN AND/OR OTHER PATIENT CONDITIONS, which is a continuation of U.S. patent application Ser. No. 14/483,061, filed Sep. 10, 2014, entitled SYSTEMS AND METHODS FOR PRODUCING ASYNCHRONOUS NEURAL RESPONSES TO TREAT PAIN AND/OR OTHER PATIENT CONDITIONS, which is a continuation of U.S. patent application Ser. No. 13/857,960, filed Apr. 5, 2013, now issued as U.S. Pat. No. 8,849,410, entitled SYSTEMS AND METHODS FOR PRODUCING ASYNCHRONOUS NEURAL RESPONSES TO TREAT PAIN AND/OR OTHER PATIENT CONDITIONS, which is a continuation application of U.S. patent application Ser. No. 13/544,727, filed Jul. 9, 2012, now issued as U.S. Pat. No. 8,509,906, entitled SYSTEMS AND METHODS FOR PRODUCING ASYNCHRONOUS NEURAL RESPONSES TO TREAT PAIN AND/OR OTHER PATIENT CONDITIONS, which is a continuation application of U.S. patent application Ser. No. 12/362,244, filed Jan. 29, 2009, now issued as U.S. Pat. No. 8,255,057, entitled SYSTEMS AND METHODS FOR PRODUCING ASYNCHRONOUS NEURAL RESPONSES TO TREAT PAIN AND/OR OTHER PATIENT CONDITIONS, which are incorporated herein by reference in their entireties.

TECHNICAL FIELD

The present disclosure is directed generally to systems and methods for producing asynchronous neural responses, such as for the treatment of pain and/or other disorders.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and in many cases, the SCS leads are implanted percutaneously through a large needle inserted into the epidural space, with or without the assistance of a stylet.

Once implanted, the pulse generator applies electrical pulses to the electrodes, which in turn modify the function of the patient's nervous system, such as altering the patient's responsiveness to sensory stimuli and/or altering the patient's motor-circuit output. In pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. Accordingly, there remains a need for improved techniques and systems for addressing patient pain.

DETAILED DESCRIPTION

A. Overview

Figure 1:
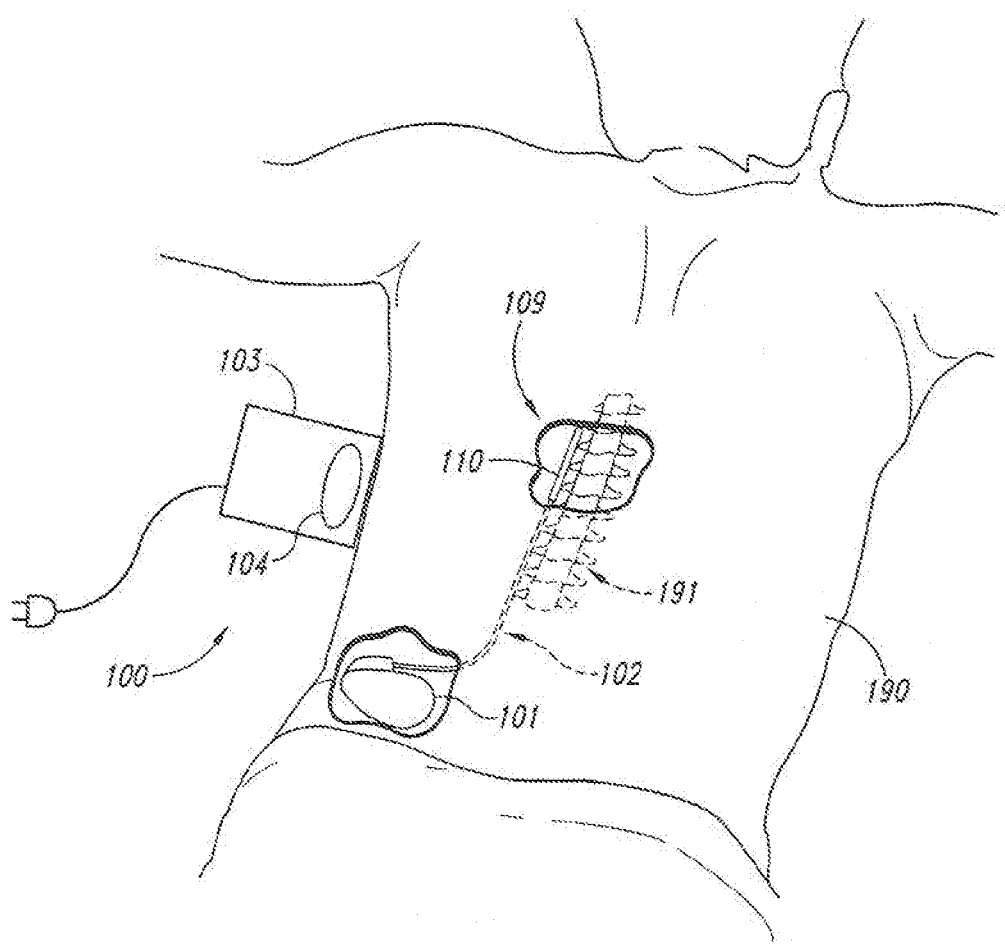
FIG. 1 is a schematic illustration of an implantable spinal cord stimulation system positioned at the spine to deliver therapeutic signals in accordance with an embodiment of the present disclosure.

The present disclosure is directed generally to systems and methods for producing asynchronous neural output or responses, such as to treat pain. Specific details of certain embodiments of the disclosure are described below with reference to methods for stimulating a target neural population or site of a patient, and associated implantable structures for providing the stimulation. Although selected embodiments are described below with reference to stimulating the dorsal root and/or other regions of the spinal column to control pain, the leads may in some instances be used for stimulating other neurological structures, and/or other tissue (e.g., muscle tissue). Some embodiments can have configurations, components or procedures different than those described in this section, and other embodiments may eliminate particular components or procedures. A person of ordinary skill in the relevant art, therefore, will understand that the invention may have other embodiments with additional elements, and/or may have other embodiments without several of the features shown and described below with reference to FIGS. 1-12.

A representative method in accordance with a particular embodiment for treating a patient's pain includes selecting a target stimulation frequency that is above a threshold frequency. The threshold frequency corresponds to a refractory period for neurons of a target sensory neural population. The method can further include producing a patient sensation of paresthesia by directing an electrical signal to multiple sensory neurons of the target sensory neural population at the target stimulation frequency. Individual neurons of the sensory neural population can complete corresponding individual refractory periods at different times, resulting in an asynchronous sensory neuron response to the electrical signals. In at least some embodiments, it is expected that this method can produce an enhanced effect for the patient, e.g. a smoother and/or a more pleasant sensation than that resulting from standard spinal cord stimulation.

In a further particular embodiment, directing the electrical signal in accordance with the foregoing method can include initiating the asynchronous sensory neuron response by directing to the target sensory neural population a generally constant stream of pulses at a frequency greater than the threshold frequency. The duration of the asynchronous sensory response can then be extended (e.g., beyond an initial period) by directing multiple electrical signals to the target sensory neural population. These signals can include a first electrical signal having pulses delivered at a first frequency that is at or above the threshold frequency, and a second electrical signal having pulses delivered at a second frequency, also at or above the threshold frequency. The pulses of the first and second signals can be interleaved, with individual pulses of the first electrical signal being followed by individual pulses of the second electrical signal, and spaced apart from the individual pulses of the first electrical signal by a first time interval less than the refractory period. Individual pulses of the second electrical signal are followed by individual pulses of the first electrical signal, and are spaced apart from the individual pulses of the first electrical signal by a second time interval that is also less than the refractory period.

B. Embodiments of Methods for Applying Neural Stimulation, and Associated Systems FIG. 1 schematically illustrates a representative treatment system 100 for providing relief from chronic pain and/or other conditions, arranged relative to the general anatomy of a patient's spinal cord 191. The system 100 can include a pulse generator 101, which may be implanted subcutaneously within a patient 190 and coupled to a signal delivery element 109. In a representative example, the signal delivery element 109 includes a lead body 110 that carries features for delivering therapy to the patient 190 after implantation. The pulse generator 101 can be connected directly to the lead body 110 or it can be coupled to the lead body 110 via a communication link 102. As used herein, the term lead body includes any of a number of suitable substrates and/or support members that carry devices for providing therapy signals to the patient 190. For example, the lead body 110 can include one or more electrodes or electrical contacts that direct electrical signals into the patient's tissue, such as to provide for patient relief. In other embodiments, the signal delivery element 109 can include devices other than a lead body (e.g., a paddle) that also direct electrical signals and/or other types of signals to the patient 190.

The pulse generator 101 can transmit signals to the signal delivery element 109 that up-regulate (e.g. stimulate) and/or down-regulate (e.g. block) target nerves. Accordingly, the pulse generator 101 can include a machine-readable (e.g., computer-readable) medium containing instructions for generating and transmitting suitable therapy signals. The pulse generator 101 and/or other elements of the system 100 can include one or more processors, memories and/or input/output devices. The pulse generator 101 can include multiple portions, elements, and/or subsystems (e.g., for directing signals in accordance with multiple signal delivery parameters), housed in a single housing, as shown in FIG. 1, or in multiple housings.

In some embodiments, the pulse generator 101 can obtain power to generate the therapy signals from an external power source 103. The external power source 103 can transmit power to the implanted pulse generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In another embodiment, the pulse generator 101 can obtain the power to generate therapy signals from an internal power source, in addition to or in lieu of the external power source 103. For example, the implanted pulse generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

In still further embodiments, an external programmer (not shown) can communicate with the implantable pulse generator 101 via electromagnetic induction. Accordingly, a practitioner can update the therapy instructions provided by the pulse generator 101. Optionally, the patient may also have control over at least some therapy functions, e.g., starting and/or stopping the pulse generator 101.

Figure 2:
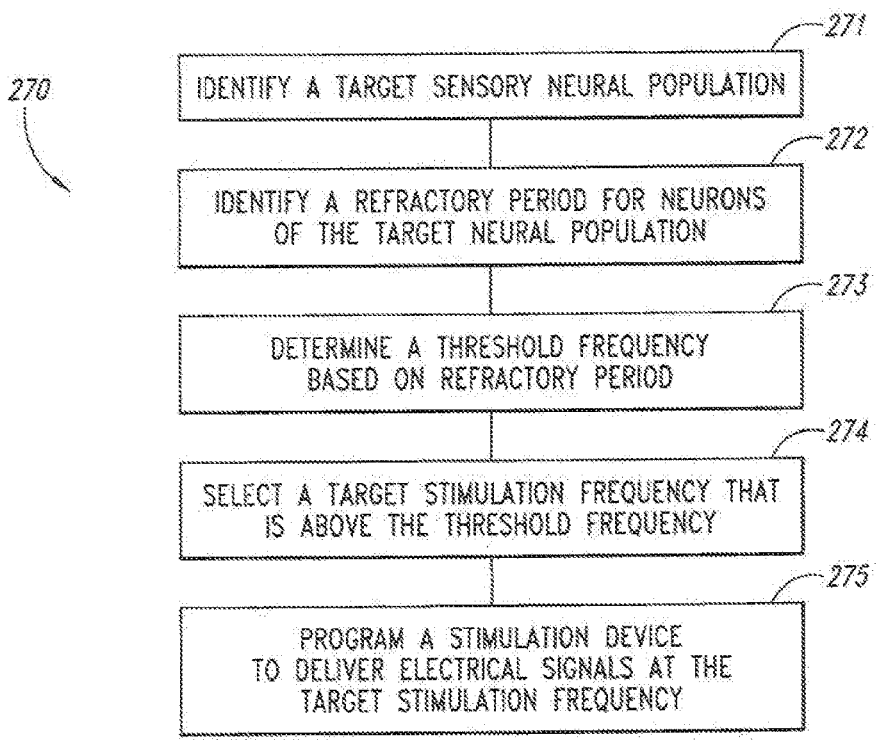
FIG. 2 is a flow diagram illustrating a process for selecting a frequency in accordance with which stimulation is provided to a patient in an embodiment of the disclosure.

FIG. 2 is a flow diagram illustrating a process 270 for selecting signal delivery parameters in accordance with an embodiment of the disclosure. Process portion 271 includes identifying a target sensory neural population. For example, the target sensory neural population can include a neural population (e.g., neural fibers) located at the spinal cord. Process portion 272 can include identifying a refractory period for neurons of the target neural population. As used herein, the refractory period refers generally to the period of time during which an activated neuron (e.g., a neuron that has fired an action potential) is unable to fire an additional action potential. The refractory period includes an absolute refractory period and a relative refractory period. The absolute refractory period refers generally to the period during which no new action potential can be produced, no matter the strength of the electrical signal applied, and the relative refractory period refers generally to the period during which a new action potential can be produced, but the stimulus strength must be increased. Unless otherwise noted, a refractory period as used herein generally refers to the entire or total refractory period, e.g., the combined absolute refractory period and relative refractory period. The refractory period can correspond to an average expected refractory period for a population of neurons, or to a refractory period of a particular neuron. The refractory period can be determined based on information obtained from a pool of patients or other generalized data, or a practitioner can determine a patient-specific refractory period. For example, the practitioner can use generalized refractory period data initially, (e.g., to establish a threshold frequency and a target frequency, as described below) and can then fine-tune the target frequency based on patient-specific requirements and/or feedback. In at least some cases, the refractory period may vary from one neural population to another. In such cases, the practitioner can identify or determine a refractory period for a specific neural population, or base an estimate for the refractory period on an established correspondence or similarity between neural populations.

Process portion 273 includes determining a threshold frequency based at least on part on the refractory period. Generally, process portion 273 includes taking the inverse of the refractory period to determine the threshold frequency. Process portion 274 can include selecting a target stimulation frequency that is above the threshold frequency. For example, the target stimulation frequency can be selected so that neighboring pulses are spaced apart by less than the total refractory period, but more than the absolute refractory period. In other embodiments, the target stimulation frequency can be selected so that neighboring pulses are spaced apart by less than the absolute refractory period. The degree to which the target stimulation frequency exceeds the threshold frequency can be selected based (at least in part) upon factors that include the nature of the target sensory neural population, patient-specific feedback, and/or others. In particular embodiments, the target stimulation frequency can be about an order of magnitude (e.g., about a factor of 10) or more above the threshold frequency. In other embodiments, the target stimulation frequency can be double the threshold frequency, or another multiple of the threshold frequency greater than or less than 2, but greater than 1. For example, in a particular embodiment, the absolute refractory period for Aß fibers has a value of from about 1 msec. to about 3 msec. (and a relative refractory period of about 1-2 msec.), corresponding to a frequency range of about 200 Hz-1,000 Hz. The corresponding target stimulation frequency can have a value of 2,000 Hz, 3,000 Hz, 5,000 Hz, 8,000 Hz or 10,000 Hz. In a further particular embodiment, it is expected that frequencies between 3,000 Hz and 10,000 Hz will produce enhanced patient benefits. These values are higher than the standard spinal cord stimulation frequency, which is generally from 2 to 1,500 Hz. The particular value of the frequency selected for a given patient can depend at least in part on patient feedback (e.g., which frequency provides the most pleasant sensation), and/or a target system power requirement, with higher frequencies generally corresponding to higher power requirements. In any of these embodiments, as a result of the selected frequency being greater than the threshold frequency, individual pulses of the electrical signal will be directed both to sensory neurons that are in refractory, and sensory neurons that are in refractory but excitable. In process portion 275, a stimulation device (e.g., a spinal cord stimulation device) is programmed to deliver the electrical signal at the target stimulation frequency.

Figure 3:
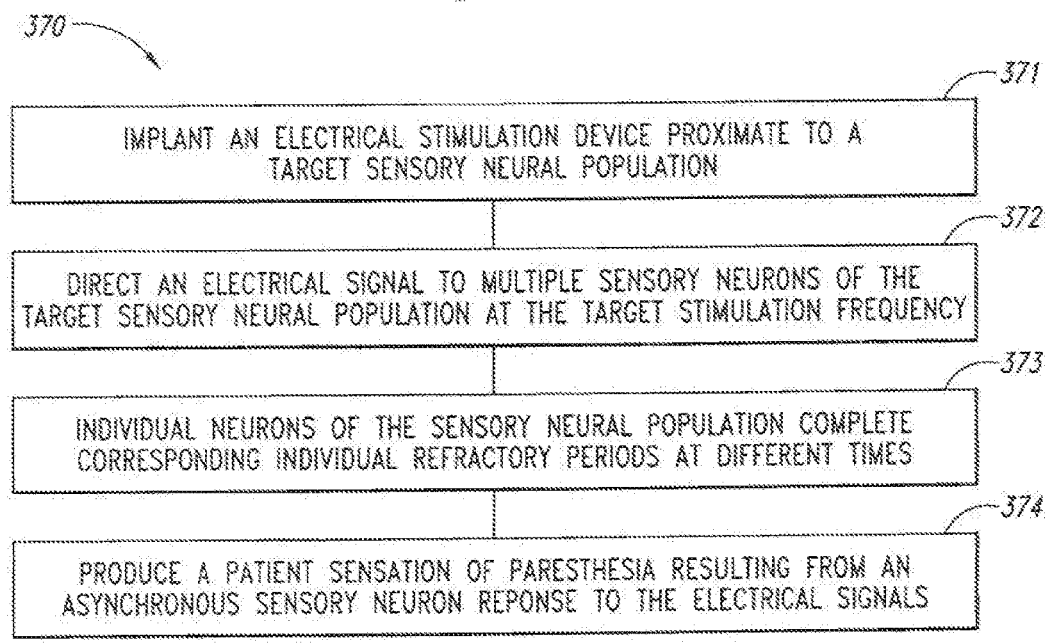
FIG. 3 is a flow diagram illustrating a representative process for treating a patient in accordance with an embodiment of the disclosure.

FIG. 3 is a flow diagram of a process 370 for treating a patient. Process portion 371 includes implanting an electrical stimulation device proximate to a target sensory neural population e.g., at the patient's spinal cord. Process portion 372 includes directing an electrical signal to multiple sensory neurons of the target sensory neural population at the target stimulation frequency. In process portion 373, individual neurons of the sensory neural population complete corresponding individual refractory periods at different times. This may result because individual neurons can have different individual refractory periods based on the size of the neuron and also because the physiological activation of sensory neurons is not synchronous across the entire population. Process portion 374 includes producing a sensation of paresthesia in the patient, resulting from an asynchronous sensory neuron response to the electrical signals. For example, by applying an electrical signal at a frequency greater than the threshold frequency, individual neurons are expected to be exposed to (and respond to) a stimulation pulse very quickly after completing corresponding individual refractory periods. Because individual neurons are completing individual refractory periods at different times, the individual neurons become reactivated at different times. This produces an asynchronous sensory neuron response that is expected to have an improved sensation for the patient. In particular, patients treated with such a stimulation signal are expected to report a smooth and/or otherwise pleasant sensation, as opposed to a rough, tingly, prickly, and/or other sensation that may not be as pleasant. In addition, it is expected that such signals will not block afferent signals from the target sensory neural population. Accordingly, in particular embodiments, the patient's ability to perceive other sensations is not expected to be affected significantly or at all. As a result, selecting the target stimulation frequency in accordance with the foregoing parameters can produce a beneficial result for the patient.

Figure 4:
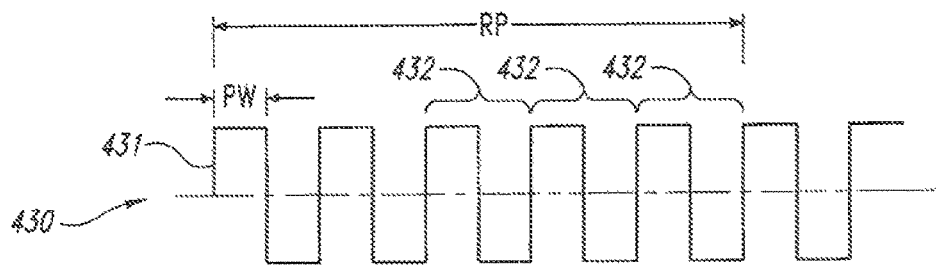
FIG. 4 is a timing diagram illustrating an electrical therapy signal having parameters selected in accordance with a representative embodiment of the disclosure.

FIG. 4 is a timing diagram illustrating a representative first signal 430 in accordance with a particular embodiment of the present disclosure. In this embodiment, the signal 430 includes a continuous string of biphasic, charge-balanced, paired pulses 431 having a pulse width PW. Each neighboring pair of anodic and cathodic pulses corresponds to a cycle 432 having a period P and an associated frequency F. Because each cycle 432 immediately follows the preceding cycle 432, the signal 430 has no interpulse interval.

As is also shown in FIG. 4, the frequency F of the signal 430 produces a period P for each cycle 432 that is significantly less than a corresponding refractory period RP. This arrangement is expected to produce the patient sensations described above with reference to FIG. 3.

Figure 5:
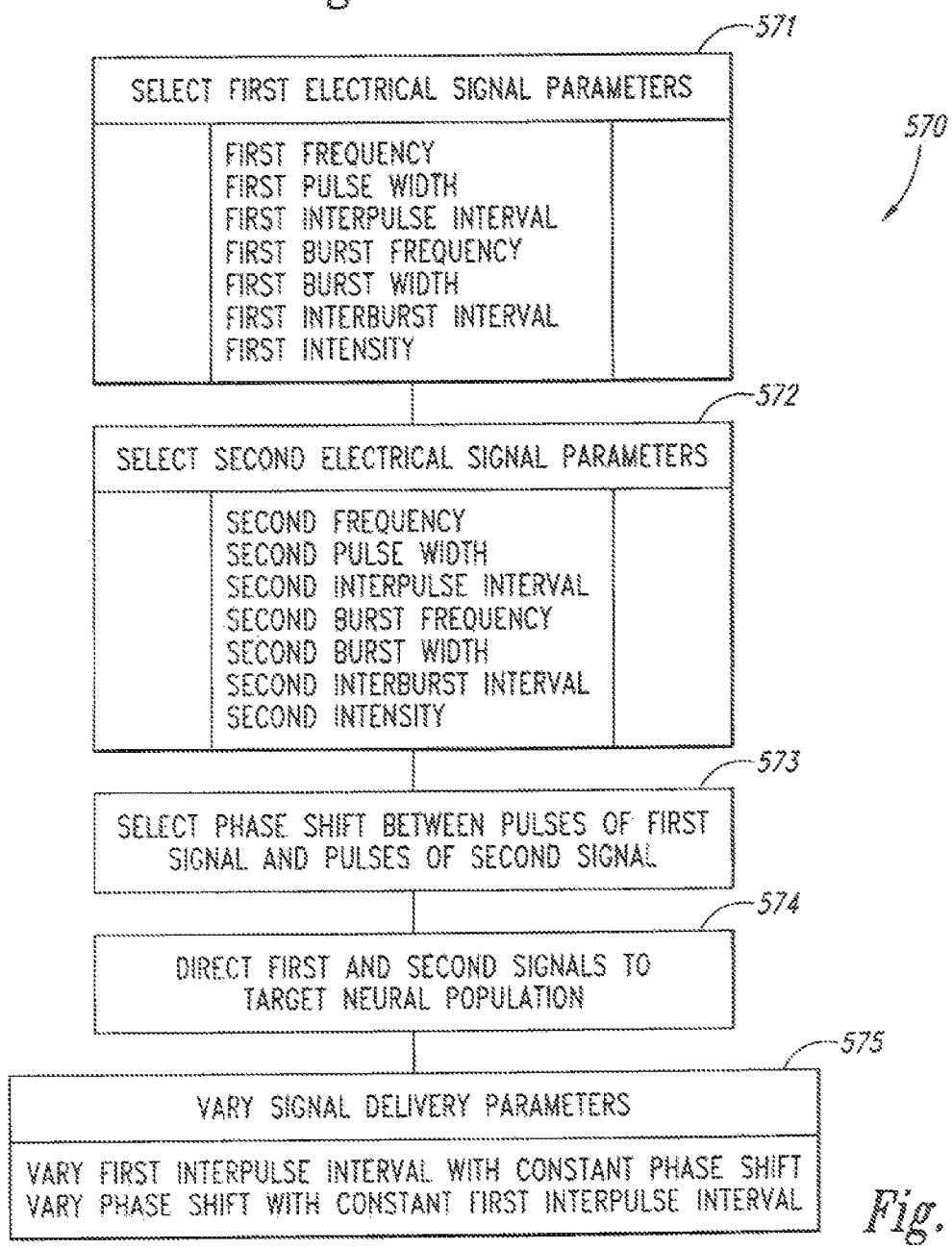
FIG. 5 is a flow diagram illustrating a process for selecting parameters for delivering multiple electrical signals in accordance with another embodiment of the disclosure.

In some cases, it may be desirable to reduce the power required to deliver the electrical signal, without significantly reducing the associated asynchronous neural response. One approach to achieving this result is to deliver multiple electrical signals, for example, two electrical signals, that together produce an asynchronous neural response, but with less power than is required to produce the continuous stream of pulses shown in FIG. 4. FIG. 5 illustrates a representative method 570 for producing such a result. The method 570 includes selecting first electrical signal parameters (process portion 571) that can include a first frequency, first pulse width, first interpulse interval, first burst frequency, first burst width, first interburst interval, and first intensity. The frequency, pulse width, and interpulse interval of the first signal are described above with reference to FIG. 4. The burst frequency refers to the frequency at which groups of pulses are delivered to the patient, and the burst width refers to the time period over which any particular group of pulses is delivered. The interburst interval refers to the time period between bursts, and the intensity refers to the amplitude (e.g., voltage and/or current) or intensity of the pulses. In a representative example, the pulses are provided at current-controlled intensity level of from about 0.1 mA to about 20 mA, and, more particularly, about 0.5 mA to about 5.0 mA, with a varying voltage of up to about 15 volts, and a frequency of about 10,000 Hz. Values toward the higher ends of the foregoing ranges may be used in particular embodiments, e.g., when sensory subcutaneous nerves and/or other sensory and/or motor peripheral nerves (as opposed to spinal nerves) form the target neural population. In a further representative example, sequential bursts can be separated from each other by less than one second, and the overall duty cycle of the first signal alone (or the first and second signals together) can be about 50%.

Process portion 572 includes selecting corresponding parameters for the second electrical signal. Process portion 573 includes selecting a phase shift or offset between pulses of the first signal and pulses of the second signal. In process portion 574, the first and second electrical signals are directed to a target neural population. Optionally, the process 570 can include varying the signal delivery parameters (process portion 575), for example, by varying the first interpulse interval with a constant phase shift between pulses of the first signal and pulses of the second signal, or by varying the phase shift with a constant first interpulse interval. Examples of representative wave forms selected in accordance with the process 570 are described below with reference to FIGS. 6-8.

Figure 6:
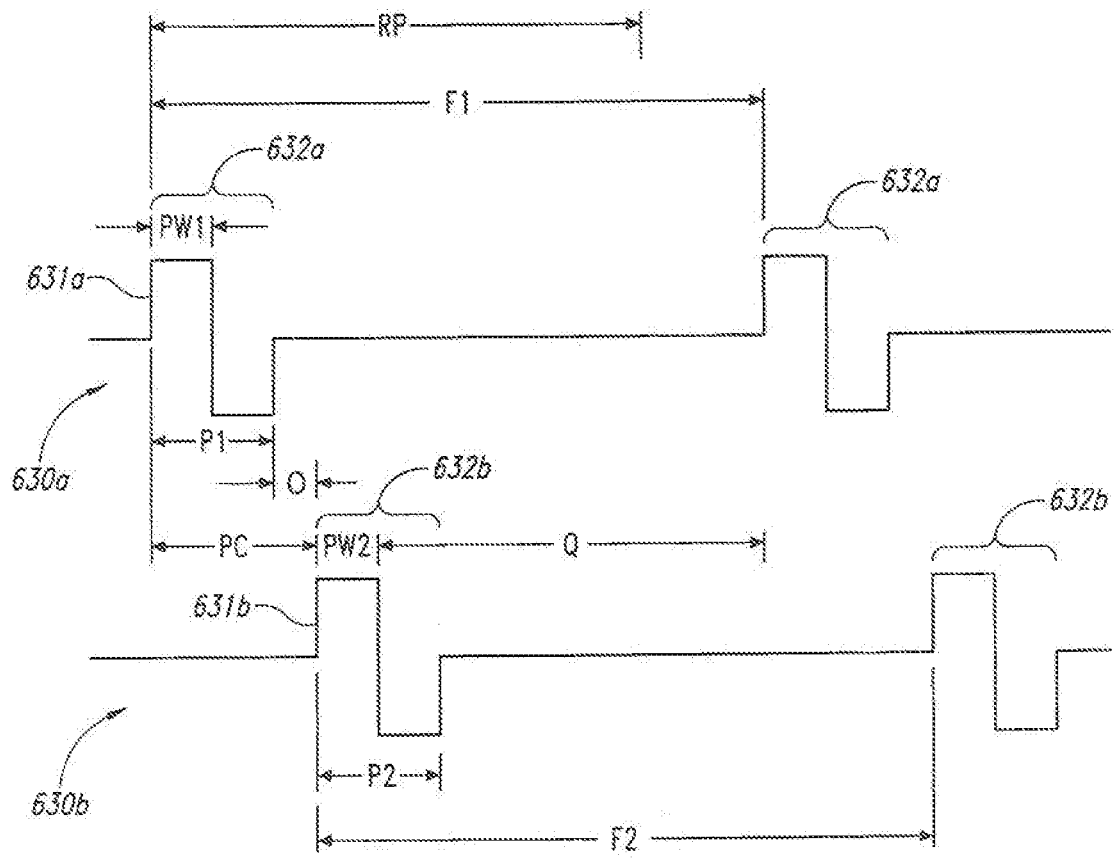
FIG. 6 is a timing diagram illustrating signal delivery parameters for two signals delivered in accordance with an embodiment of the disclosure.

FIG. 6 is a timing diagram illustrating wave forms for two electrical signals, shown as a first electrical signal 630*a* and a second electrical signal 630*b*. The first electrical signal 630*a* includes first cycles 632*a*, each of which includes a first pulse 631*a* having a pulse width PW1. Individual first cycles 632*a* have a first period P1. The second electrical signal 630*b* includes multiple second cycles 632*b*, each of which includes a second pulse 632*b* having a second pulse width PW2. Individual second cycles 632*b* have a second period P2.

In a particular embodiment, each second cycle 632*b* of the second signal 630*b* follows a corresponding first cycle 632*a* of the first signal 630*a*, and is spaced apart from the first cycle 632*a* by an offset or phase shift O. In particular embodiments, the offset O can have a constant value, so that the first and second frequencies F1, F2 are equal. In other embodiments, the offset O can vary, which can prolong the effectiveness of the therapy. It is believed that one possible mechanism by which the therapy effectiveness can be prolonged is by reducing the patient's maladaptive response, e.g., by reducing a tendency for the patient's central nervous system to lessen its response to the effects of a non-varying signal over time. In still further embodiments, it is expected that the practitioner can reduce the patient's maladaptive response without varying signal delivery parameters, and/or via a treatment regimen that includes more than two electrical signals or only a single electrical signal. For example, in at least some embodiments, applying a single, constant frequency signal (e.g., as shown in FIG. 4) so as to produce an asynchronous neural response, can reduce the maladaptive response of the patient's central nervous system, e.g., when compared with a signal that produces a synchronous neural response.

The combination of the first signal 630*a* and the second signal 630*b* produces a combined period PC corresponding to the first period P1 plus the offset O. In a particular aspect of this embodiment, the combined period PC is selected to be smaller than the refractory period RP. However, the first frequency F1 may be selected to be slower than the corresponding total refractory period. If the first signal 630*a* alone were provided to the patient in accordance with these parameters, it would not likely produce an asynchronous neural response. However, the second signal 630*b* can supplement the effects of the first signal 630*a*. In particular, the second pulses 631*b* are delivered in a manner that activates neurons that may come out of their refractory periods after the preceding first pulse 631*a*. This is expected to be the case because the combined period PC is less than the refractory period RP. For example, the combined period PC can be a suitable fraction (e.g., one-half or one-third) of the total refractory period RP. These values can be less than the total refractory period, but greater than the absolute refractory period. In a particular embodiment, the total refractory period RP can have a value of about 2-4 msec., and the first and second frequencies F1, F2 can have a value of from about 250 Hz to about 500 Hz. The combined period PC can have a value of from about 50 μsec. to about 300 μsec. and in a particular embodiment, about 100 μsec.

In operation, the first and second signals 630*a*, 630*b* may be applied to the patient after the constant pulses described above with reference to FIG. 4 are applied. Accordingly, the constant pulse pattern shown in FIG. 4 can be used to establish an initial asynchronous neural response, for example, over a time period of several microseconds to several seconds, e.g., several milliseconds. This asynchronous response period can be extended by the first and second signals 630*a*, 630*b*, without expending the amount of power required to produce a continuous stream of pulses over the same period of time. The power savings can result because the combination of the first and second signals 630*a*, 630*b* produces a quiescent period Q during which no pulses are applied to the patient. In general, it is expected that the quiescent period Q will be less than or equal to the refractory period RP. As a result, the patient benefit is expected to at least approach the benefit achieved with the constant stream of pulses shown in FIG. 4. For example, in a particular embodiment, it is expected that the patient can achieve the same or nearly the same benefit whether the stimulation is in the form of a continuous stream of pulses at 3 kHz, or two overlaid sets of spaced-apart pulses, each provided at less than 1.5 kHz, with the latter stimulation requiring less power than the former.

In at least some embodiments, the amplitude of the second signal 630*b* may be greater than that of the first signal 630*a*. It is expected that the increased amplitude of the second signal 630*b* may be more effective at activating neurons that are in a relative refractory state rather than an absolute refractory state, thus reducing the number of neurons available to fire during the quiescent period Q. In general, it is expected that using two signals to achieve the foregoing pulse-to-pulse amplitude variation is more readily achievable with two overlaid signals than with a single signal, at least for particular stimulation parameters (e.g., at high frequencies). Paired signals with different amplitudes can also more readily activate smaller Aβ fibers. In general, the signals are preferentially directed to Aβ fibers over C fibers. In general, the signals are also preferentially directed so as to avoid triggering a muscle response. In addition to, or in lieu of, the increased amplitude, the second signal 630*b* can have pulses with a second pulse width PW2 greater than the first pulse width PW1. The particular values of the signal amplitude, pulse width and/or other parameters can be selected based at least in part on patient feedback. In any of these embodiments, this arrangement can further extend the asynchronous neural response established by the initial constant pulse pattern described above.

Figure 7:
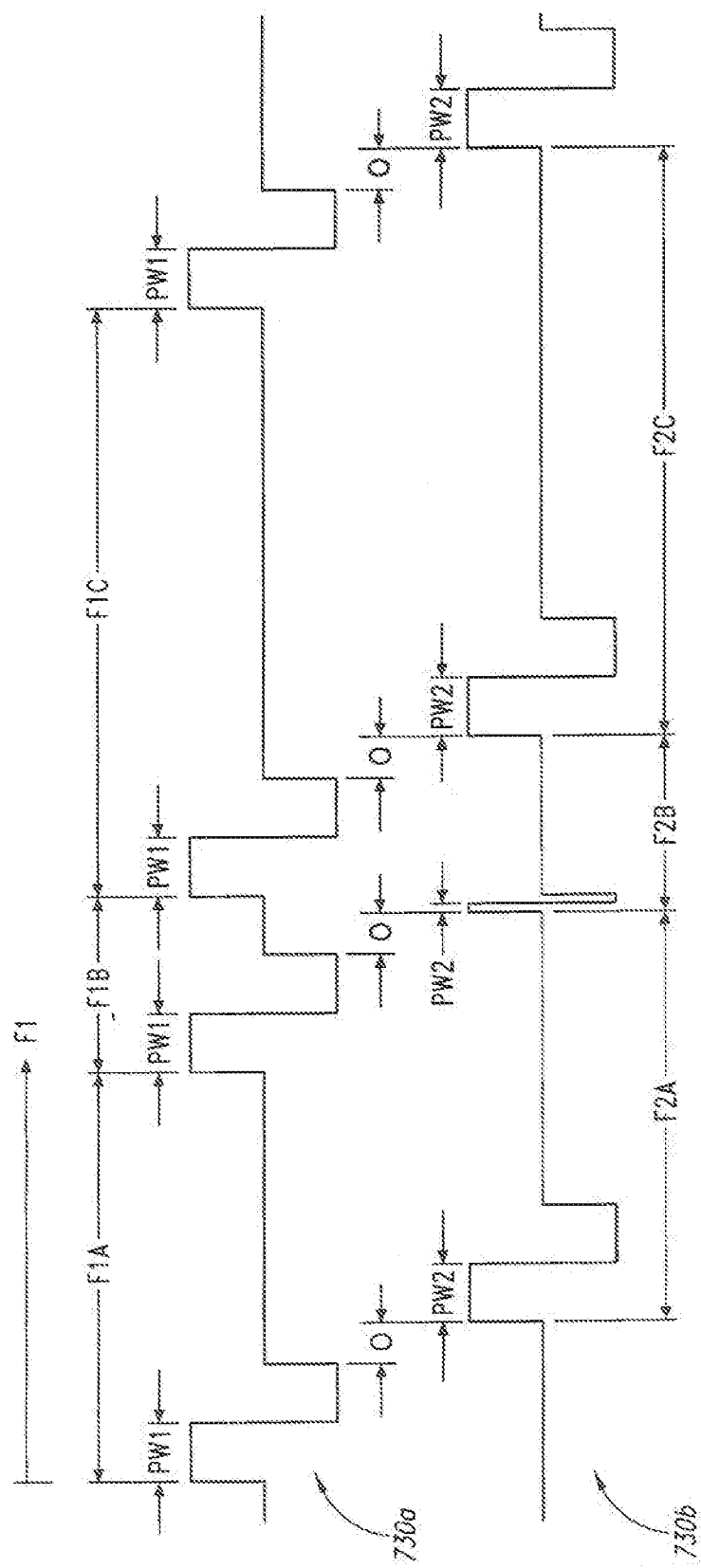
FIG. 7 is a timing diagram illustrating parameters for delivering two signals in accordance with another embodiment of the disclosure.

FIG. 7 is a timing diagram illustrating wave forms for two electrical signals, shown as a first electrical signal 730*a* and a second electrical signal 730*b*, having parameters selected in accordance with another embodiment of the disclosure. The two electrical signals 730*a*, 730*b* are generally similar to the corresponding first and second electrical signals 630*a*, 630b described above with reference to FIG. 6, except that the first frequency F1 and the second frequency F2 both vary, as indicated by frequencies F1A-F1C and F2A-F2C. For example, the first frequency F1 initially increases (as pulses become closer together) and then decreases. The second frequency F2 also decreases and then increases. In a particular aspect of this embodiment, the offset or phase shift O between pulses of the first electrical signal 730a and pulses of the second electrical signal 730b remains constant despite the changes in the first and second frequencies F1, F2. In some cases, this can produce a varying pulse width PW2 for the second signal 730b. For example, the second pulse of the second signal 730b shown in FIG. 7 has a reduced pulse width PW2 compared with the pulse width of either the first or third pulse, in order to fit between the second and third pulses of the first signal 730a. This arrangement can prevent the pulses of the two signals 730a, 730b from overlapping each other. One potential advantage of the varying first and second electrical signals 730a, 730b shown in FIG. 7 is that this arrangement can reduce the likelihood for the patient to develop a maladaptive response to a constant set of signals, while still producing an asynchronous patient response, with a reduced power requirement, as discussed above with reference to FIG. 6.

Figure 8:
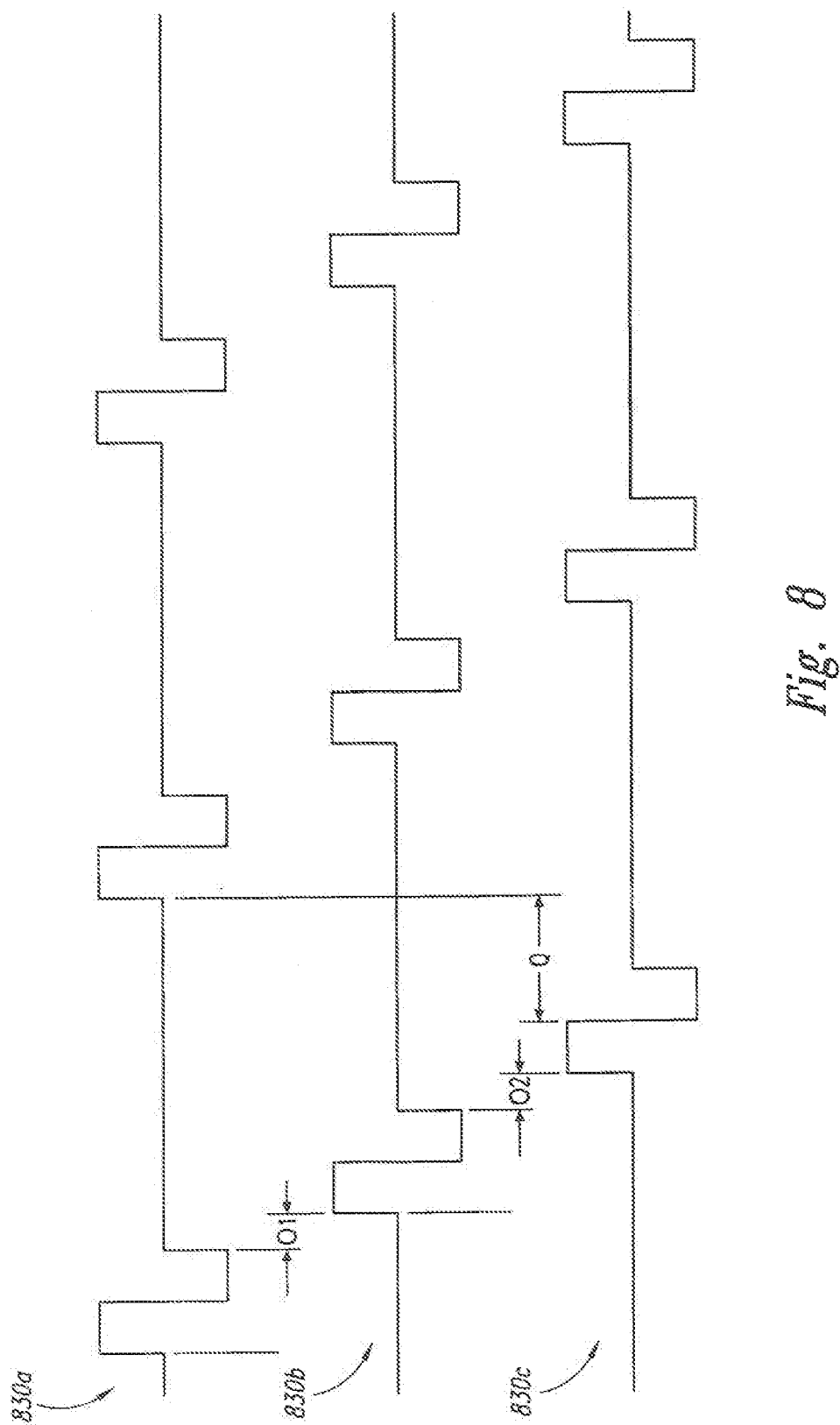
FIG. 8 is a timing diagram illustrating a process for delivering three signals in accordance with still another embodiment of the disclosure.

In other embodiments, the patient can receive stimulation from more than two signals. For example, as shown in FIG. 8, the patient can receive three electrical signals, shown as a first electrical signal 830a, a second electrical signal 830b, and a third electrical signal 830c. Pulses of the second electrical signal 830b can be offset from corresponding pulses of the first electrical signal 830a by a first offset O1, and pulses of the third electrical signal 830c can be offset from pulses of the second electrical signal 830b by a second offset O2. By superposing the three electrical signals, the patient can feel sensations generally similar to those described above with reference to FIG. 6 or 7, with a power savings similar in principle (though perhaps not value) to those described above. In particular, the superposition of three signals may provide a smoother effect for the patient with slightly less power savings than are expected from superposing two signals.

Figure 9:
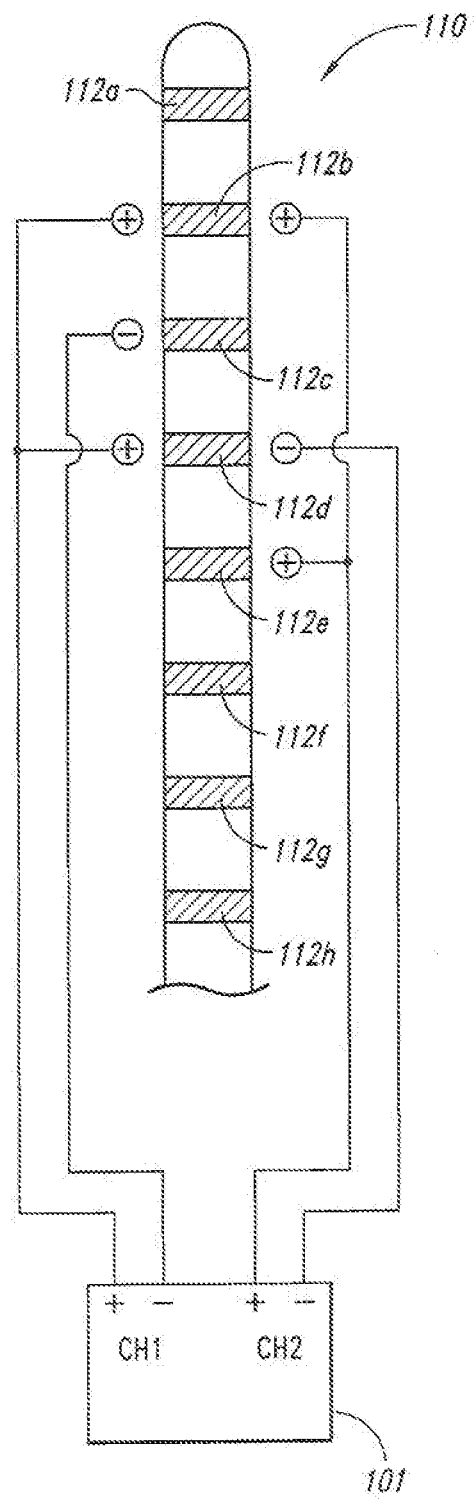
FIG. 9 is a schematic illustration of an electrode configured to deliver two signals in accordance with an embodiment of the disclosure.

FIG. 9 is a partial schematic illustration of a representative lead body 110 coupled to a controller 101 in accordance with a particular embodiment of the disclosure. In this embodiment, the lead body 110 includes eight electrodes 112a-112h, and the controller 101 includes two channels, CH1 and CH2. A cathodal signal is applied from the first channel CH1 to the third electrode 112c, and an anodal signal is applied from the first channel CH1 to the second and fourth electrodes 112b, 112d. The second channel CH2 applies a cathodal signal to the fourth electrode 112d, and an anodal signal to the second and fifth electrodes 112b, 112e. In one aspect of this embodiment, at least one of the electrodes to which the second channel CH2 is coupled is different than the electrodes to which the first channel CH1 is coupled. Accordingly, the portion of the overall target neural population receiving the pulses from the second channel CH2 can be different than (though perhaps overlapping with) the portion of the target neural population receiving pulses from the first channel CH1. It is expected that in at least some embodiments this will increase the number of neurons at the overall target neural population that respond asynchronously. In addition to or in lieu of this effect, it is expected that the electrical field produced by the second channel CH2 will differ more significantly from that produced by the first channel CH1 when it is produced by a different set of electrodes, which can also increase the likelihood of an asynchronous neural response. In other embodiments, signals applied to the channels can be varied in other manners, in addition to or in lieu of the foregoing arrangement, including but not limited to switching individual electrodes from cathodic to anodic or vice versa.

Figure 10:
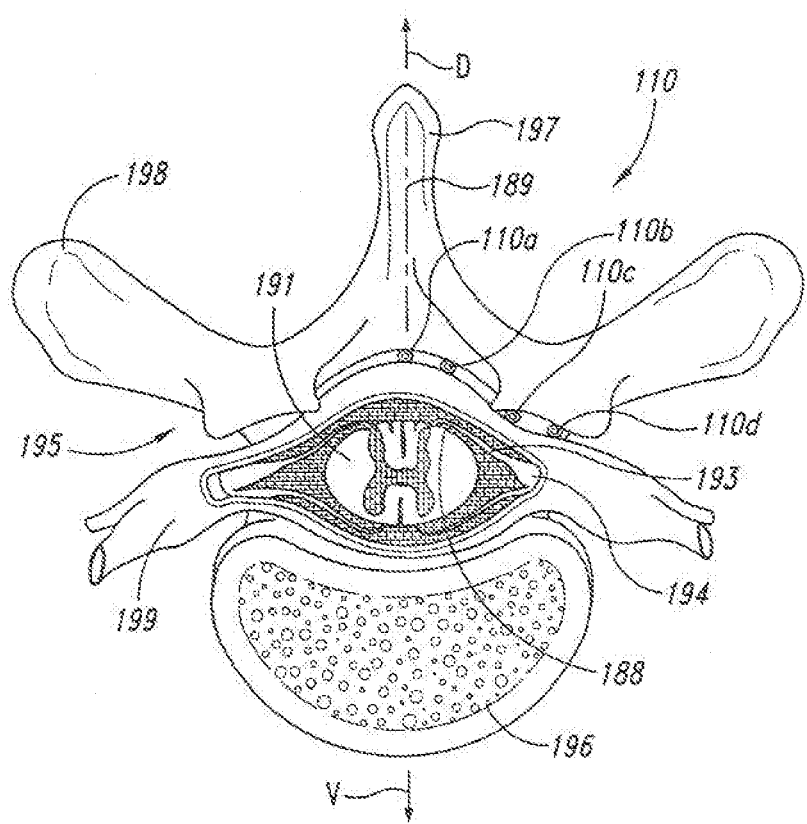
FIG. 10 is a partially schematic, cross-sectional illustration of a patient's spine illustrating representative locations for implanted lead bodies in accordance with an embodiment of the disclosure.

FIG. 10 is a cross-sectional illustration of the spinal cord 191 and an adjacent vertebra 195 (based generally on information from Crossman and Neary, "Neuroanatomy," 1995 (publ. by Churchill Livingstone)), along with selected representative locations for representative lead bodies 110 (shown as lead bodies 110a-110d) in accordance with several embodiments of the disclosure. The spinal cord 191 is situated between a ventrally located vertebral body 196 and the dorsally located transverse process 198 and spinous process 197. Arrows V and D identify the ventral and dorsal directions, respectively. In particular embodiments, the vertebra 195 can be at T10 or T11 (e.g., for axial low back pain or leg pain) and in other embodiments, the lead bodies can be placed at other locations. The spinal cord 191 itself is located within the dura mater 199, which also surrounds portions of the nerves exiting the spinal cord 191, including the dorsal roots 193 and dorsal root ganglia 194. The lead body is generally positioned to preferentially stimulate tactile fibers and to avoid stimulating fibers associated with nociceptive pain transmission. In a particular embodiment, a lead body 110a can be positioned centrally in a lateral direction (e.g., aligned with the spinal cord midline 189) to provide signals directly to the spinal cord 191. In other embodiments, the lead body can be located laterally from the midline 189. For example, the lead body can be positioned just off the spinal cord midline 189 (as indicated by lead body 110b), and/or proximate to the dorsal root 193 or dorsal root entry zone 188 (e.g., 1-4 mm from the spinal cord midline 189, as indicated generally by lead body 110c), and/or proximate to the dorsal root ganglion 194 (as indicated by lead body 110d). Other suitable locations for the lead body 110 include the "gutter," also located laterally from the midline 189, and the dorsal root entry zone. In still further embodiments, the lead bodies may have other locations proximate to the spinal cord 191 and/or proximate to other target neural populations e.g., laterally from the midline 189 and medially from the dorsal root ganglion 194.

Figure 11:
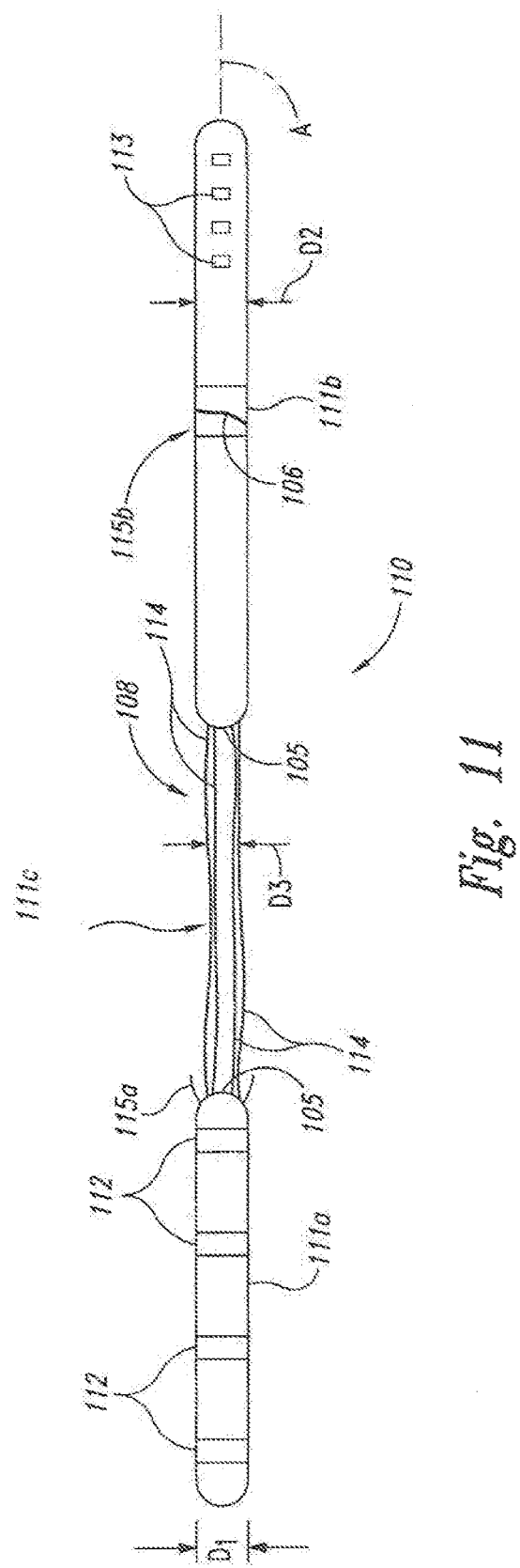
FIG. 11 is a partially schematic illustration of a lead body configured in accordance with another embodiment of the disclosure.

FIG. 11 is a partially schematic, side elevation view of a lead body 110 configured in accordance with another embodiment of the disclosure. The lead body 110 can include a first or distal portion 111a, a second or proximal portion 111b, and an intermediate third portion 111c located between the first and second portions 111a, 111b. The first portion 111a can carry signal delivery electrodes 112, or other features configured to deliver therapeutic signals to the patient. The second portion 111b can include connection terminals 113 or other features configured to facilitate communication with the implantable pulse generator 101 (FIG. 1). The third portion 111c can include a link, e.g., an electrical link 108 having multiple wires 114 that provide signal communication between the connection terminals 113 of the second portion 111b and the signal delivery electrodes 112 of the first portion 111a.

The first portion 111a can include signal delivery electrodes 112 that have an annular or ring shape and are exposed at the outer circumferential surface of the first portion 111a, as shown in FIG. 11. In other embodiments, the signal delivery electrodes 112 can have other configurations, e.g., the electrodes 112 can have a flat or curved disc shape. The first portion 111a can have an overall diameter D1 which is sized to allow the first portion 111a to pass through the lumen of a delivery catheter or other delivery device. The first portion 111a can also include a first fixation device 115a to secure or at least partially secure the first portion 111a in position at a target site. In a particular embodiment, the first fixation device 115a can include one or more tines, or an annular cup that faces proximally (rightward as shown in FIG. 11) to resist axial motion. In other embodiments, the first fixation device 115a can include other features.

The second portion 111b can include the connection terminals 113 described above, and can have an overall diameter D2. In a particular embodiment, the diameter D2 of the second portion of 111b can be approximately the same as the diameter D1 of the first portion of 111a. The second portion 111b can include a second fixation device 115b, for example, one or more sutures 106 that secure or at least partially secure the second portion 111b in position. Each of the first and second portions 111a, 111b can include rounded, convex external surfaces 105 (e.g., at the proximal end of the first portion 111a and/or at the distal end of the second portion 111b) that are exposed to patient tissue and, due to the rounded shapes of these surfaces, facilitate moving the lead body 110 in the patient's body. The third portion 111c can have a diameter D3 that is less than the diameters D1, D2 of the first and second portions 111a, 111b, and a stiffness less than a stiffness of the first and second portions 111a, 111b. Accordingly, the third portion 111c can be flexible enough to allow the second portion 111b to move without disturbing the position of the first portion 111a. Further details of the lead body 110 shown in FIG. 11 are included in pending U.S. patent application Ser. No. 12/129,078, filed May 29, 2008 and incorporated herein by reference.

Figure 12:
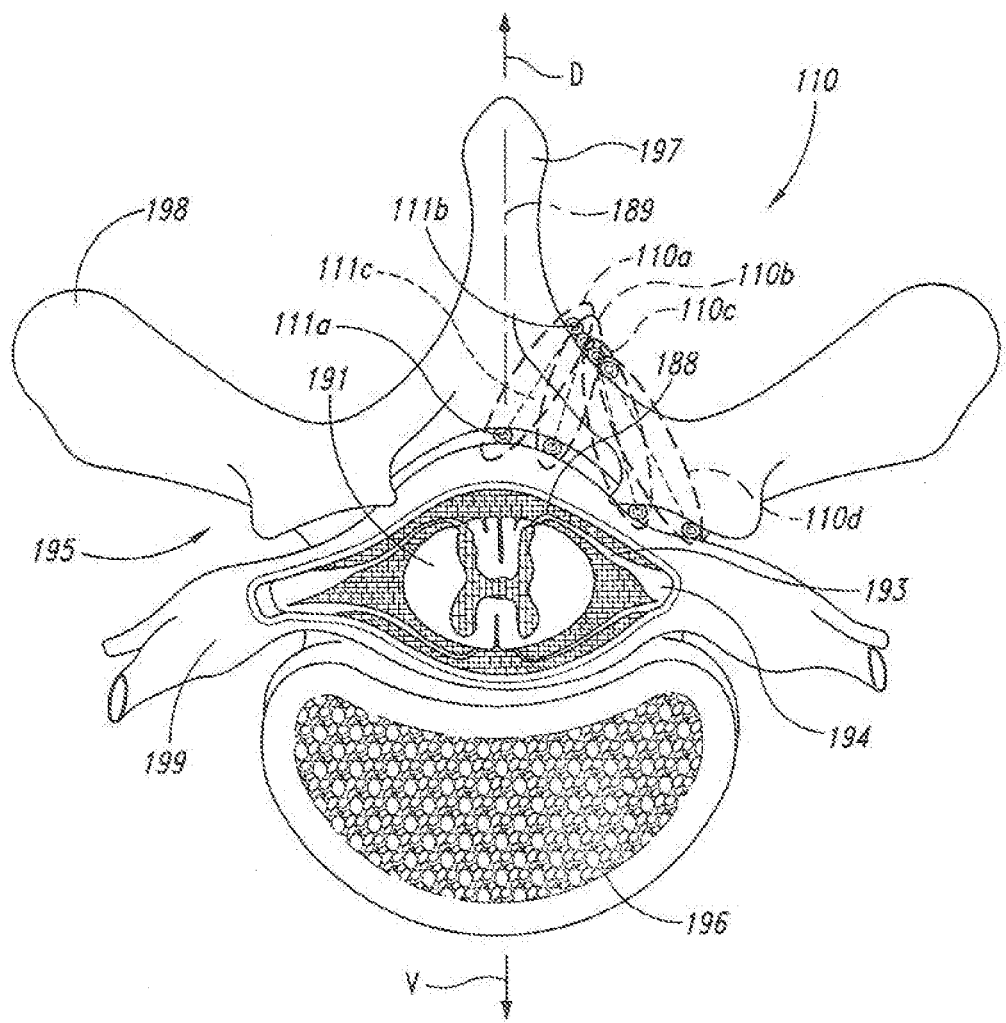
FIG. 12 is a partially schematic, cross-sectional illustration of the patient's spine illustrating representative locations for implanted lead bodies in accordance with still further embodiments of the disclosure.

FIG. 12 is a cross-sectional illustration of the spinal cord 191 and an adjacent vertebra 195 along with selected representative locations for representative lead bodies 110 generally similar to those described above with reference to FIG. 11 and shown in FIG. 12 as lead bodies 110a-110d. In each of the foregoing representative locations, the first portion 111a of the lead body 110 can be positioned epidurally (or subdurally) proximate to a target neural population at the spinal cord 191 while the second portion 111b is positioned radially outwardly from the spinal cord 191, and while the third portion 111c provides a flexible coupling between the first and second portions. The first portion 111a can be positioned relative to the spinal cord 191 at locations generally similar to those described above with reference to FIG. 10.

In a particular embodiment, the practitioner can use an automated (e.g., computer-implemented) or semi-automated feedback technique to select the particular frequency or frequencies of signals applied to a patient. In one aspect of this embodiment, treatment leads can be placed at any of the locations shown in FIG. 10 or 12 in the patient's lower back region, for example, at T10. The practitioner can also outfit the patient with one or more diagnostic leads (e.g., epidural recording leads) located at the gutter, but at a superior position along the spine. For example, the practitioner can position two epidural recording leads in the gutter, one on each side of the midline, at a cervical location. The diagnostic leads are not expected to discriminate between action potentials from individual neurons, but rather can record an overall action potential sum. At low stimulation frequencies, in response to which the neuron population generates synchronous action potentials, the recorded signal strength of the compound action potential is expected to be higher than when the patient produces asynchronous responses at higher frequencies, in which the recorded signal will have a lower signal strength indicating fewer additive action potentials.

Accordingly, in one embodiment, the practitioner can increase the frequency of the signals applied to the treatment leads, while observing the amplitude of the summed compound action potential response recorded by the recording leads. When the detected response decreases, this can indicate to the practitioner that the patient is generating asynchronous action potentials. This information can be used alone or in combination with a patient response to select a longer term stimulation frequency. In a particular embodiment, the practitioner can start at a low frequency (e.g., about 40 Hz) and, using an automated program, increase the frequency of the stimulation applied to the patient up to a level of about 10,000 Hz. The program can then automatically decrease the frequency in accordance with one or more set increments until the detected response increases to or changes by a threshold level (which the program can detect automatically), and/or the patient indicates a change. The patient's reported change may include an indication that the patient's perceived sensation is no longer smooth and is instead rough, or otherwise less desirable.

In other embodiments, other aspects of the foregoing operation can be automated. For example, the system can automatically identify a baseline signal strength corresponding to a synchronous response. In a particular embodiment, the baseline signal strength can be the signal strength recorded when the patient is stimulated at 40 Hz or another low frequency. As the system automatically increases the stimulation frequency to identify an appropriate frequency for eliciting an asynchronous response, it compares the recorded signal strengths with the baseline level. If the recorded signal strength is equal to or higher than the baseline level, the patient response is identified as a synchronous response. If the recorded signal strength is lower than the baseline level, then the patient response is identified as asynchronous or transitioning to asynchronous. At this point, the system can automatically vary the frequency (increasing and/or decreasing) in a closed loop manner to identify a target frequency (e.g., an optimum frequency) that the patient will receive during therapy. In a particular embodiment, the target frequency is the frequency that produces the most asynchronous patient response.

One feature of many of the foregoing embodiments described above is the application of one or more electrical signals to the patient's neural tissue that produce an asynchronous response. As described above, it is expected that an asynchronous response will produce a smoother or otherwise more pleasant patient sensation than standard spinal cord stimulation, while still masking or otherwise beneficially altering pain signals. In addition, particular embodiments are expected to reduce power consumption by providing intermittent or otherwise spaced-apart signals that are nevertheless timed to trigger an asynchronous patient response. By reducing the power consumption of the device, these embodiments can decrease the frequency with which the patient recharges the implanted stimulator, and/or decrease the frequency with which a non-rechargeable battery within the implanted stimulation must be replaced. The intermittent signal may also produce other patient benefits, possibly including an increase in the term over which the therapy is effective.

From the foregoing, it will be appreciated that specific embodiments of the disclosure have been described herein for purposes of illustration, but that various modifications may be made without deviating from the invention. For example, the wave forms of the electrical signals applied to the patient may have characteristics other than those specifically shown and described above. In a particular example, the wave forms may include pulses other than square wave pulses. In other embodiments, the leads or other signal delivery devices may have configurations other than those specifically shown and described above. Furthermore, while certain embodiments were described in the context of spinal cord stimulation, generally similar techniques may be applied to other neural populations in other embodiments using similar and/or modified devices. For example, stimulation signals selected to produce an asynchronous patient response can be applied subcutaneously to peripheral nerves. Such nerves can include occipital nerves, which can be stimulated to address headaches and/or facial and/or neck pain, and/or peripheral nerves at the lower back to address lower back pain. In still further embodiments, the stimulation signals can be applied to neural populations to produce an asynchronous response that addresses patient conditions other than pain. In another embodiment, such signals can be applied to the autonomic nervous system, e.g., to the splenic nerve to address obesity. In any of the foregoing cases, the refractory periods and threshold frequencies may differ from those associated with spinal cord stimulation, but the methodologies used to select the target stimulation frequency can be generally the same or similar.

Certain aspects of the invention described in the context of particular embodiments may be combined or eliminated in other embodiments. For example, a given signal delivery protocol may include different signals at different times during a treatment regimen, with the signals having characteristics generally similar to any of those described above with reference to FIGS. 4 and 6-8. Characteristics of particular signals (e.g., the first signal) may be applied to other signals (e.g., the second signal, and/or a continuous pulse stream, such as that shown in FIG. 4). Further, while advantages associated with certain embodiments have been described in the context of those embodiments, other embodiments may also exhibit such advantages. Not all embodiments need necessarily exhibit such advantages to fall within the scope of the present disclosure. Accordingly, the invention can include other embodiments not specifically shown or described above.

We claim:

1. A method for automatically adjusting stimulation delivered to a patient, the method comprising:
    applying an electrical stimulation signal to a neural population of a patient to evoke a neural response generated by the neural population, wherein the electrical stimulation signal has a first parameter value;
    measuring, via an implanted signal detection device, the neural response evoked by the applied electrical stimulation signal;
    comparing the measured neural response to a prior level; and
    after comparing the measured neural response to the prior level, automatically adjusting the first parameter value to a second parameter value based at least in part on the measured neural response.

2. The method of claim 1, further comprising repeating, in a closed loop manner, the operations of applying, measuring, comparing, and adjusting until a target neural response is measured.

3. The method of claim 1 wherein the evoked neural response is an asynchronous response.

4. The method of claim 1 wherein measuring the neural response includes measuring a compound action potential of the neural population, and wherein comparing the measured neural response includes comparing the compound action potential to the prior level.

5. The method of claim 4 wherein comparing the compound action potential to the prior level is performed in part to determine whether the neural population is generating asynchronous action potentials.

6. The method of claim 1 wherein the prior level is a baseline level.

7. The method of claim 6 wherein the baseline level corresponds to a synchronous neural response generated by the neural population.

8. The method of claim 1 wherein adjusting the first parameter value includes adjusting a frequency of the electrical stimulation signal to be at or above 40 Hz.

9. The method of claim 1 wherein the signal detection device includes one or more diagnostic leads.

10. The method of claim 1 wherein the signal detection device is positioned proximate a spinal cord of the patient.

11. The method of claim 1 wherein measuring the neural response includes directly measuring the neural response.

12. A system for applying neural stimulation to a patient, the system comprising:
    an implantable pulse generator configured to generate an electrical stimulation signal having at least a first parameter value;
    an electrode array having one or more electrodes coupleable to the pulse generator; and
    a sensor coupleable to the pulse generator and configured to be positioned proximate an anatomical feature of the patient,
    wherein the pulse generator includes a machine-readable medium having instructions that, when executed, cause the pulse generator to—
        deliver the electrical stimulation signal to a neural population of the patient via the one or more electrodes;
        sense, via the sensor, a neural response generated by the neural population in response to the delivered electrical stimulation signal;
        determine a feedback value based on the sensed neural response generated by the neural population; and
        based on the determined feedback value, automatically adjust the first parameter value of the electrical stimulation signal to a second parameter value different than the first parameter value.

13. The system of claim 12 wherein the feedback value corresponds to a relationship between the sensed neural response and a baseline level.

14. The method of claim 12, further comprising iteratively performing the operations of delivering, sensing, determining, and automatically adjusting in a closed loop until a target neural response is sensed.

15. The method of claim 12 wherein the first and second parameter values each correspond to frequencies, and wherein automatically adjusting includes automatically decreasing a frequency of the delivered electrical stimulation signal by a preset increment until the sensed neural response increases to or changes by a threshold value.

16. The method of claim 12 wherein the neural response is an action potential generated by the neural population.

17. The method of claim 12 wherein the neural response is a compound action potential representing a sum of individual action potentials.

18. The system of claim 12 wherein the sensor includes one or more implantable epidural recording leads positioned adjacent the anatomical feature of the patient.

19. A method for delivering closed loop neuromodulation, the method comprising:

applying an electrical stimulation signal, having a first parameter value, to a neural population to evoke a neural response;

directly measuring, via an implanted sensor, the neural response evoked by the applied electrical stimulation signal;

comparing the measured neural response to a baseline level;

after comparing the measured neural response, adjusting the first parameter value to a second parameter value based at least in part on the measured neural response, wherein the first parameter value differs from the second parameter value; and iteratively performing the operations of applying, measuring, comparing, and adjusting until a target neural response is measured.

20. The method of claim 19 wherein adjusting the first parameter value includes automatically adjusting one or more of a frequency, amplitude, pulse width, and/or current.

21. The method of claim 19 wherein the neural response corresponds to an action potential generated by the neural population.

22. The method of claim 19 wherein adjusting the first parameter value includes adjusting a frequency of the electrical stimulation signal to be in a range from 3 kHz to 10 kHz.

* * * * *